United States Patent

Hamprecht et al.

Patent Number: 5,840,904
Date of Patent: Nov. 24, 1998

[54] FLUORO-PYRIDINE-2,3-DICARBOXYLIC ANHYDRIDES WHICH ARE INTERMEDIATES FOR HERBICIDAL PYRIDINE-2,3-DICARBOXIMIDES

[75] Inventors: Gerhard Hamprecht, Weinheim; Eberhard Fuchs, Frankenthal; Matthias Gerber, Limburgerhof; Helmut Walter, Obrigheim; Karl-Otto Westphalen, Speyer, all of Germany

[73] Assignee: BASF Aktiengesellschaft, Ludwigshafen, Germany

[21] Appl. No.: 863,540

[22] Filed: May 27, 1997

Related U.S. Application Data

[62] Division of Ser. No. 361,559, Dec. 22, 1994, Pat. No. 5,679,622.

[51] Int. Cl.$^6$ .............................................. C07D 491/048
[52] U.S. Cl. .............................................. 546/116
[58] Field of Search .............................................. 546/116

[56] References Cited

U.S. PATENT DOCUMENTS 5,262,384   11/1993   Hamprecht et al. .................... 504/225

*Primary Examiner*—Bernard Dentz
*Attorney, Agent, or Firm*—Keil & Weinkauf

[57] ABSTRACT

Pyridine-2,3-dicarboximides of the general formula I

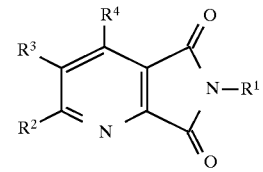

where
$R^1$ is hydrogen, alkoxy or unsubstituted or substituted alkyl, cycloalkyl, alkenyl or alkynyl and $R^2$, $R^3$ and $R^4$ are identical or different and are each hydrogen, halogen, cyano, unsubstituted or substituted alkyl, benzyl, cycloalkyl, alkenyl, alkynyl, alkoxy, phenoxy or phenylthio, a 5-membered or 6-membered heterocyclic radical having one or two hetero atoms selected from the group consisting of oxygen, sulfur and nitrogen, or unsubstituted or substituted phenyl, with the proviso that
a) $R^2$ is fluorine and $R^3$ and $R^4$ have the abovementioned general meanings or
b) $R^3$ is fluorine, chlorine, $C_1$–$C_3$-alkoxy, $C_2$–$C_5$-alkenyloxy, $C_2$–$C_5$-alkynyloxy, trifluoromathyl or cyano and $R^2$ and $R^4$ have the abovementioned general meanings or
c) $R^4$ is halogen or $C_1$–$C_3$-alkoxy, $C_2$–$C_5$-alkenyloxy or $C_2$–$C_5$alky-nyloxy and $R^2$ and $R^3$ have the abovementioned general meanings, with the exception of 5-chloropyridine-2,3-dicarboximide, and the environmentally compatible salts thereof.

2 Claims, No Drawings

FLUORO-PYRIDINE-2,3-DICARBOXYLIC ANHYDRIDES WHICH ARE INTERMEDIATES FOR HERBICIDAL PYRIDINE-2,3-DICARBOXIMIDES

This is a divisional of application Ser. No. 08/361,559, filed Dec. 22, 1994 now U.S. Pat. No. 5,629,622.

The present invention relates to pyridine-2,3-dicarboximides of the formula I

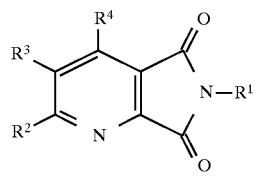

where $R^1$ is hydrogen;

$C_1$–$C_4$-alkoxy;

$C_1$–$C_6$-alkyl which may carry from one to three of the following groups: $C_1$–$C_4$-alkoxy, $C_1$–$C_4$-halcoalkoxy, $C_1$–$C_4$-alkylthio, $C_1$–$C_4$-haloalkylthio, $C_1$–$C_4$-dialkylamino, $C_3$–$C_8$-cycloalkyl or halogen;

$C_3$–$C_8$-cycloalkyl which may carry from one to three of the following groups: $C_1$–$C_6$-alkyl, $C_1$–C6-haloalkyl, $C_1$–$C_4$-alkoxy, $C_1$–C4-haloalkoxy, halogen or nitro;

$C_3$–$C_6$-alkenyl or $C_3$–$C_6$-alkynyl which may be monosubstituted to trisubstituted by halogen, and $R^2$, $R^3$ and $R^4$ are identical or different and are each hydrogen, halogen, cyano, $C_1$–$C_6$-alkyl which may be substituted by from one to five halogen atoms and/or one or two of the following radicals: $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl or cyano;

benzyl which may be monosubstituted to trisubstituted by $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

$C_3$–$C_8$-cycloalkyl which may be monosubstituted to trisubstituted by $C_1$–$C_4$-alkyl or halogen;

$C_2$–$C_6$-alkenyl which may be monosubstituted to trisubstituted by halogen and/or monosubstituted by $C_1$–$C_3$-alkoxy or by phenyl which may carry from one to three of the following groupst $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthiol halogen, cyano or nitro;

$C_2$–$C_6$-alkynyl which may be monosubstituted to trisubstituted by halogen or $C_1$–$C_3$-alkoxy and/or monosubstituted by phenyl which may carry from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

$C_1$–$C_4$-alkoxy, $C_1$–$C_4$-alkylthio, $C_1$–$C_4$-haloalkoxy, $C_1$–$C_4$-haloalkylthio, $C_2$–$C_5$-alkenyloxy, $C_2$–$C_5$-alkynyloxy, $C_1$–$C_4$-alkylsulfinyl, $C_1$–$C_4$-alkylsulfonyl, $C_1$–$C_4$-haloalkylsulfonyl;

phenoxy or phenylthio, each of which may be monosubstituted to trisubstituted by $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

a 5-membered or 6-membered heterocyclic radical having one or two hetero atoms selected from the group consisting of oxygen, sulfur and nitrogen, which may carry one or two substituents of the following group: $C_1$–$C_3$-alkyl, halogen, $C_1$–$C_3$-alkoxy or $C_2$–$C_4$-alkoxycarbonyl or phenyl which may carry from one to three of the following groups: $C_1$–$C_6$-alkyl, $C_f$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, halogen, nitro or cyano, with the proviso that a) $R^2$ is fluorine and $R^3$ and $R^4$ have the abovementioned general meanings or b) $R^3$ is fluorine, chlorine, $C_1$–$C_3$-alkoxy, $C_2$–$C_5$-alkenyloxy, $C_2$–$C_5$-alkynyloxy, trifluoromethyl or cyano and $R^2$ and $R^4$ have the abovementioned general meanings or c) $R^4$ is halogen, $C_1$–$C_3$-alkoxy, $C_2$–$C_5$-alkenyloxy or $C_2$–$C_5$-alkynyloxy and $R^2$ and $R^3$ have the abovementioned general meanings, with the exception of 5-chloropyridine-2,3-dicarboximide, and the environmentally compatible salts thereof.

The present invention furthermore relates to processes for the preparation of the compounds I and their use for controlling undesirable plant growth. The present invention also relates to novel pyridine-2,3-dicarboxylates and pyridine-2,3-dicarboxylic anhydrides, in particular fluorine-substituted in each case, which are used as intermediates for the preparation of the compounds I.

N-Substituted pyridinedicarboximides and the derivatives thereof are known. EP-A 128 006 describes, inter alia, N-cycloalkylene-pyridinedicarboximides and their use as soil fungicides.

U.S. Pat. No. 3,539,568 describes a process for the preparation of 2,3- and 3,4-pyridinedicarboximides and their conversion to isomeric dicarboxamides, which can be used as intermediates for herbicidal pyrimidinediones.

U.S. Pat. No. 4,261,730 discloses 3-carboxypyridine-2-N-(aryl)carboxamides and phthalamic acids having growth-regulating activity.

U.S. Pat. No. 4,658,030 discloses a process for the preparation of herbicidal 2-(imidazolin-2-yl)-nicotinic acids based on 3-carboxypyridine-2-(N-2-carbamido-3-methyl-2-butyl)-carboxamides.

Helv. Chim. Acta 71 (1988), 486 and 493 discloses a cycloaddition process for the preparation of pyridine-2,3-dicarboximides.

J 5 7085-386 describes specifically substituted pyridine-2,3-dicarboximides having antitumor activity.

Herbicidal pyridine-2,3-dicarboximides are disclosed in EP-A 422 456.

The following prior art is relevant with respect to the novel intermediates: J. Med. Chem. 17, 1065 discloses 5-chloropyridine-2,3-dicarboximide. Halogen-substituted anhydrides, such as 5-halopyridine-2,3-dicarboxylic anhydride, eg. 5-chloropyridine-2,3-dicarboxylic anhydride or perfluoropyridine-2,3-dicarboxylic anhydride, are disclosed in Chemical Abstracts, Vol. 84, 135440, and Vol. 55, 23525, and Chem. Ber. 56, 2457. Individual pyridine-2,3-dicarboxylates and pyridine-2,3-dicarbonyl chlorides are described in Chemical Abstracts, Vol. 206, 213955, DE-A 36 34 975, EP-A 227 932 and EP-A 299 362.

It is an object of the present invention to provide pyridine-2,3-dicarboximides having improved biological activity, in particular better selectivity and high herbicidal activity.

We have found that this object is achieved by the pyridine-2,3-dicarboximides defined at the outset.

Pyridine-2,3-dicarboximides of the formula I, where $R^1$ is hydrogen, $C_1$–$C_6$-alkyl, $C_3$–$C_6$-alkenyl, $C_3$–$C_6$-alkynyl, 1-(cyclopropyl)-$C_1$–$C_3$-alkyl, 1-$C_1$–$C_2$-alkylcyclopropyl or $C_3$–$C_6$-cycloalkyl and two of the three radicals $R^2$, $R^3$ or $R^4$ in the pyridine ring, independently of one another, are hydrogen or $C_1$–$C_4$-alkyl which may be substituted by from one to five halogen atoms, or are $C_1$–$C_4$-alkoxy, halogen or cyano, while the third substituent a) is fluorine in the case of $R^2$ (ie. the 6 position), b) is fluorine, chlorine, $C_1$–$C_3$-alkoxy, $C_2$–$C_5$-alkenyloxy, $C_2$–$C_5$-alkynyloxy, halogen, trifluoromethyl or cyano in the case of $R^3$ (ie. the 5 position) or c) is halogen or $C_1$–$C_3$-alkoxy, $C_2$–$C_5$-alkenyloxy or $C_2$–$C_5$-alkynyloxy in the case of $R^4$ (ie. the 4 position), are preferred.

Particularly preferably, at least one of the radicals $R^2$, $R^3$ or $R^4$ is halogen, in particular fluorine or chlorine. Compounds in which the pyridine ring is monosubstituted or disubstituted are also preferred. The substituent $R^1$ at the imide nitrogen is preferably alkyl, in particular branched alkyl, such as isopropyl, sec-butyl or tert-butyl, or 1-cycloalkyl-$C_1$–$C_3$-alkyl, such as 1-cyclopropylmethyl, 1-cyclopropylethyl or 1-cyclopropylpropyl.

The present invention furthermore relates to novel intermediates, such as anhydrides and fluorine-substituted pyridine-2,3-dicarboxylates. The following compounds may be mentioned here:

Pyridine-2,3-dicarboxylic anhydrides of the formula IIa'

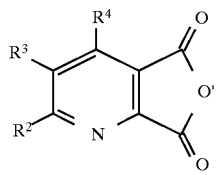

IIa where one of the radicals $R^2$, $R^3$ or $R^4$ is fluorine and the remaining radicals are each hydrogen, fluorine, chlorine, $C_1$–$C_3$-alkyl, $C_1$–$C_3$-alkoxy, trifluoromethoxy, chlorodifluoromethoxy, methylthio, trifluoromethylthio, chlorodifluoromethylthio or methylsulfonyl, with the exception of 5-fluoro- and 4,5,6-trifluoropyridine-2,3-dicarboxylic anhydride.

Particularly interesting intermediates are 6-fluoropyridine-2,3-dicarboxylic anhydride and 5,6-difluoropyridine-2,3-dicarboxylic anhydride.

Other preferred novel compounds are pyridine-2,3-dicarboxylic anhydrides of the formula IIa'

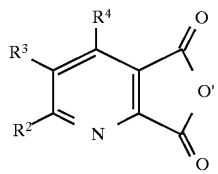

IIa where $R^4$ is hydrogen, $R^3$ is chlorine, $C_1$–$C_3$-alkoxy, trifluoromethyl or cyano and $R^2$ is fluorine, chlorine, $C_1$–$C_3$-alkyl, $C_1$–$C_3$-alkoxy, trifluoromethoxy, chlorodifluoromethoxy, methylthio, trifluoromethylthio, chlorodifluoromethylthio or methylsulfonyl or $R^2$ and $R^4$ are each hydrogen and $R^3$ is $C_1$–$C_3$-alkoxy, trifluoromothyl, cyano, trifluoromethoxy, chlorodifluoromethoxy, methylthio, trifluoromethylthio, chlorodifluoromethylthio or methylsulfonyl.

Novel intermediates at the dialkyl ester stage are dialkyl 4,5- and/or 6-fluoropyridine-2,3-dicarboxylates of the formula Va' and dialkyl esters of the formulae Va'' and Va''':

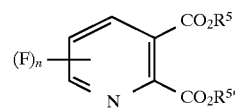

Va where n is 1, 2 or 3 and $R^5$ is $C_1$–$C_4$-alkyl, $C_3$–$C_5$-alkenyl or $C_3$–$C_5$-alkynyl, each of which is unsubstituted or substituted by halogen, phenyl or $C_1$–$C_4$-alkoxy,

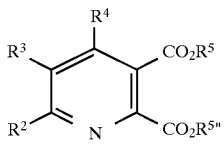

Va where one of the radicals $R^2$, $R^3$ or $R^4$ is fluorine and the remaining radicals are each hydrogen, chlorine, $C_1$–$C_3$-alkyl, $C_1$–$C_3$-alkoxy, trifluoromethoxy, chlorodifluoromethoxy, methylthio, trifluoromethylthio, chlorodifluor methylthio or methylsulfonyl and $R^5$ is $C_2$–$C_4$-alkyl, $C_3$–$C_5$-alkenyl or $C_3$–$C_5$-alicynyl, each of which is unsubstituted or substituted by halogen, phenyl or $C_1$–$C_4$-alkoxy, and

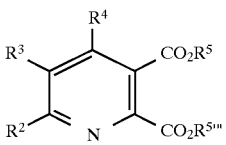

Va where $R^3$ is chlorine, methyl, $C_1$–$C_3$-alkoxy or cyano and $R^2$ and $R^4$ are each chlorine, $C_1$–$C_3$-alkyl, $C_1$–$C_3$-alkoxy, methylthio or methylsulfonyl, with the exception of diethyl 4,5-dimethyl- and 5,6-dimethylpyridine-2,3-dicarboxylate, and furthermore $R^2$ and $R^4$ are each hydrogen if $R^3$ is $C_1$–$C_3$-alkoxy, and $R^5$ is $C_2$–$C_4$-alkyl, $C_3$–$C_5$-alkenyl or $C_3$–$C_5$-alkynyl each of which is unsubstituted or substituted by halogen, phenyl or $C_1$–$C_4$-alkoxy.

The pyridine-2,3-dicarboximides of the formula I can form addition salts with inorganic acids or with alkyl halides or, if one of the substituents has acidic properties, said pyridine-2,3-dicarboximides can be reacted with inorganic and organic bases to give salts. The present invention also relates to the corresponding salts.

Examples of suitable basic salts are those of the alkali metals, preferably the sodium and potassium salts, those of the alkaline earth metals, preferably calcium, magnesium and barium salts, and those of the transition metals, preferably manganese, copper, zinc and iron salts, and the ammonium salts which may carry from one to three $C_1$–$C_4$-alkyl or hydroxy-$C_1$–$C_4$-alkyl substituents and/or one phenyl or benzyl substituent, preferably diisopropylammonium, tetramethylammonium, tetrabutylammonium, trimethylbenzylammonium and trimethyl-(2-hydroxyethyl)-ammonium salts, the phosphonium salts, the sulfonium salts, preferably tri-($C_1$–$C_4$-)alkylsulfonium salts, and the sulfoxonium salts, preterably tri-($C_1$–$C_4$-)alkylsulfoxonium salts.

Where the substitution pattern in the pyridine-2,3-dicarboximide I leads to optically active compounds, the present invention relates to the (+) and (−) enantiomers in addition to the racemates.

The pyridine-2,3-dicarboximides of the formula I can be prepared by various methods, which are described in EP-A 422 456.

According to the invention, pyridine derivatives of the formula I are obtained by reacting a pyridinedicarboxylic anhydride II

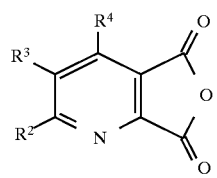

in an inert organic solvent with a primary amine III (preferably in about stoichiometric amounts)

to give a pyridinedicarboxylic acid hemiamide IV

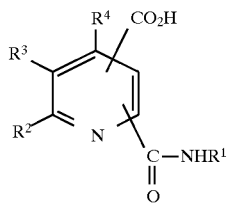

and subjecting the latter to a cyclization reaction with water-eliminating agents to give I.

We have also found chemically unique processes for the preparation of the compounds Ia,

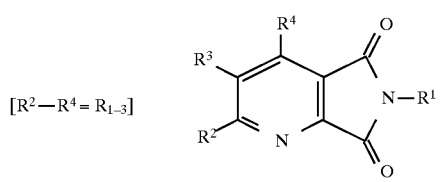

where $R^2$ to $R^4$ have the abovementioned meanings, at least one of the radicals $R^2$ to $R^4$, two of the radicals $R^2$ to $R^4$ or all radicals $R^2$ to $R^4$ being fluorine. Compared with the prior art, the pyridine derivatives Ia can be prepared in high yield and purity if a pyridine derivative Ib,

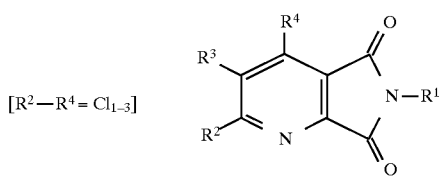

where $R^1$ to $R^4$ have the abovementioned meanings, at least one of the radicals $R^2$ to $R^4$ being chlorine or two or all of the radicals $R^2$ to $R^4$ being chlorine, is subjected to a halogen exchange reaction with potassium fluoride.

In the course of the preparation of the novel compounds, it has furthermore been found that pyridine derivatives of the formula Ia are also advantageously obtained if pyridinedicarboxylic anhydrides of the formula IIb

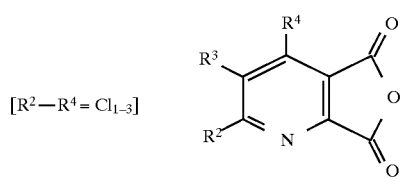

where $R^2$ to $R^4$ have the abovementioned meanings, at least one of the radicals, two of the radicals or all radicals $R^2$ to $R^4$ being chlorine, are used as starting materials and are subjected to a halogen exchange reaction with potassium fluoride to give pyridinedicarboxylic anhydrides IIa

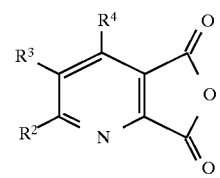

where $R^2$ to $R^4$ have the abovementioned meanings, at least one of the radicals or two or all radicals $R^2$ to $R^4$ being fluorine, and these are then converted into the pyridine derivatives Ia with a substituted amine in the manner described.

The preparation of the pyridinedicarboxylic acid hemiamides IV is advantageously carried out by a method in which the anhydride II in an inert solvent is initially taken and roughly molar amounts of an amine III, if necessary also dissolved in an inert solvent, are added dropwise. After the end of the reaction, the reaction product is filtered off with auction or is isolated by evaporating down the solvent used, the hemiamides IV being obtained.

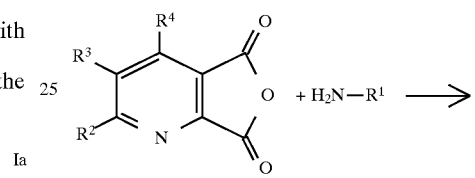

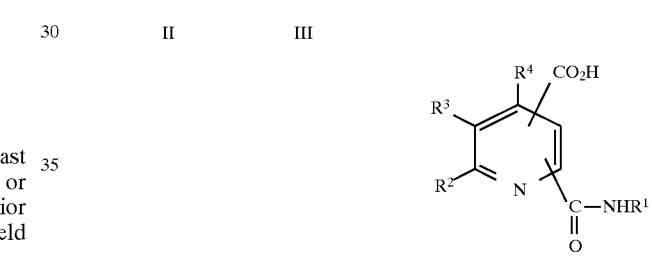

Solvents such as halohydrocarbons, eg. tetrachloroethane, methylene chloride, chloroform, chlorobenzene and 1,2-dichlorobenzene, ethers, eg. diethyl ether, methyl tert-butyl ether, dimethoxyethane, diethylene glycol dimethyl ether, tetrahydrofuran ran and dioxane, dipolar aprotic solvents, eg. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one, aromatics, eg. benzene, toluene, xylene, pyridine and quinoline, ketones, eg. acetone and methyl ethyl ketone, and corresponding mixtures are advantageously used for these reactions.

The reaction may be carried out at from −10° C. to the reflux temperature of the particular solvent or solvent mixture, preferably at from −20° to 120° C.

The molar ratios in which the required starting compounds are reacted with one another are preferably from 0.9:1 to 3:1 for the ratio of amine III to anhydride II. The concentration of the starting materials in the solvent is, for example, from 0.1 to 5, preferably from 0.2 to 2, mol/l.

The pyridinedicarboxylic acids, pyridinedicarboxylates and pyridinedicarboxylic anhydrides required as starting materials for this process are commercially available, known from the literature or can be prepared by generally known methods. A survey appears in Beilstein H 22, 150–160, E I 531–536, E II 104–111, H 27, 261, E I 319, E II 299, R. C.

Elderfield, Heterocyclic compounds, Vol. I, Chapter 8, J. Wiley and Sons, New York, E. Klingberg, Pyridine and its Derivatives, Part 3, Chapter X, in The Chemistry Of Heterocyclic Compounds, 1962 Interscience Publishers, and in EP-A 299 362 and EP-A 422 456.

These methods and methods described in EP-A 422 456 can furthermore be used to prepare novel 4- and 6-halogen- and 4,6-dihalogen-substituted pyridine-2,3-dicarboxylates by reacting corresponding 4-H-, 6-H- or 4-H-6-H-pyridine-2,3-dicarboxylic ester N-oxides with phosphoryl halides. In the course of the rearrangement reaction, the halogen first migrates to the free 6 position; if this is occupied, the halogen enters the 4 position.

The cyclization of the hemiamides IV is carried out by dehydration using a conventional water-eliminating agent, for example acetic anhydride or an inorganic acid halide, such as thionyl chloride, phosgene, phosphorous trichloride or phosphorous pentachloride, to give the pyridine derivatives of the formula I. The reaction is advantageously carried out by a method in which the carboxamides in an inert organic solvent are initially taken and the water-eliminating agent, if necessary also dissolved in an inert solvent, eq. dimethylformamide (DMF), is added dropwise. The mixture can be worked up in a conventional manner, for example by carrying out hydrolysis with water and filtering off the product with suction or extracting it with an organic solvent and evaporating the organic solvent:

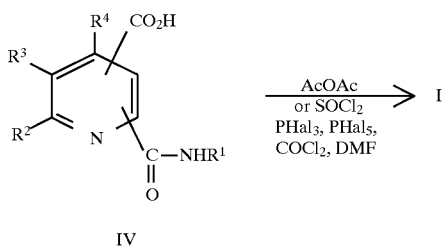

IV

Solvents such as halohydrocarbons, eg. tetrachloroethane, methylene chloride, chloroform, chlorobenzene and 1,2-dichlorobenzene, ethers, eg. diethyl ether, methyl tert-butyl ether, dimethoxyethane, diethylene glycol dimethyl ether, tetrahydrofuran and dioxane, dipolar aprotic solvents, eg. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one, aromatics, eg. benzene, toluene, xylene, pyridine and quinoline, ketones, eg. acetone and methyl ethyl ketone, and corresponding mixtures are advantageously used for these reactions.

The reaction can be carried out at from −10° C. to the reflux temperature of the particular solvent, preferably from 0° to 150° C.

The molar ratios in which the starting compounds are reacted with one another are in general from 0.9:1 to 5:1 for the ratio of the water-eliminating agent to acid amide.

The concentration of the starting materials in the solvent (mixture) is in general from 0.1 to 5, preferably from 0.2 to 2, mol/l.

A particularly advantageous process for the preparation of compounds Ia in which at least one of the radicals $R^2$ to $R^4$ is fluorine or 2 or 3 of the radicals are fluorine comprises halogen exchange of a correspondingly chlorine-substituted pyridine derivative Ib with potassium fluoride.

The reaction is preferably carried out by treating a pyridine derivative Ib in the presence of a polar solvent with potassium fluoride at from 70° to 250° C., preferably from 80° to 200° C.

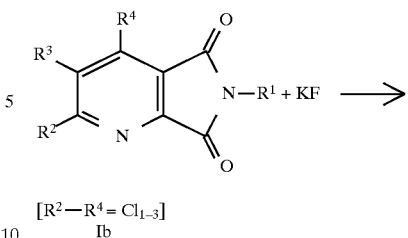

Ib

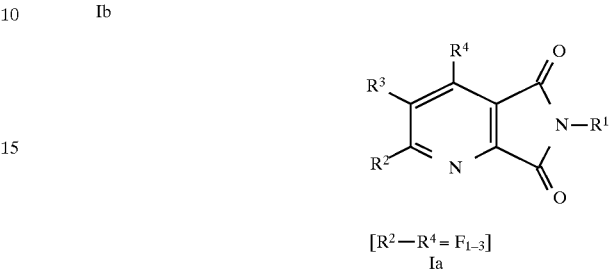

Ia

The solvents used for these reactions are nitrites, such as acetonitrile, propionitrile, butyronitrile and isobutyronitrile, glycol ethers, such as dimethyl glycol ether, diethyl glycol ether and diethylene glycol dimethyl ether, carboxamides, such as DMF and N-methylpyrrolidone, ureas, such as tetraethylurea, tetrabutylurea, dimethyleneurea and dimethylpropyleneurea, sulfoxidqs, such as dimethyl sulfoxide, and preferably sulfones, such as dimethyl sulfone, diethyl sulfone, tetramethylene sulfone (sulfolane) and pentamethylene sulfone. The procedure in the melt without the addition of a solvent is also possible according to the invention.

The halogen exchange takes place at a high rate even in the absence of a catalyst. However, it can be accelerated by adding a catalyst, for example a crown ether or cryptand. These are organic complex ligands which are particularly useful for binding alkali. The cryptands give a three-dimensional envelope. With regard to the preparation of these substances, refer to Kontakte (1977), pages 11 to 31 and 36 to 48. Preferred catalysts are crown ethers, examples of which are the following compounds: 12-crown-4, 14-crown-4, dibenzo-14-crown-4, 18-crown-5, 18-crown-6, dibenzo-18-crown-6 and aza-18-crown-6.

These catalysts are advantageously used in an amount of from 0.05 to 5, in particular from 0.1 to 2, mol percent per mole of starting material Ib.

The molar ratios in which the starting compounds are reacted with one another are from 0.9:1 to 2.0:1, preferably from 1.11 to 1.3:1, for the ratio of potassium fluoride to pyridine derivative Ib. The concentration of the starting materials in the solvent is from 0.1 to 5, preferably from 0.2 to 2, mol/l.

The compounds Ia can be particularly advantageously prepared if, before the actual halogen exchange, the pyridine derivative Ib is treated, for example in the presence of an aliphatic sulfone at up to 150° C., advantageously from 50° to 120° C., in particular from 70° to 100° C., with from 0.1 to 0.4, advantageously from 0.15 to 0.3, mol of a chloride of sulfurous acid or carbonic acid, and the reaction mixture is then reacted with potassium fluoride at from 70° to 250° C., preferably from 80° to 200° C.

Suitable catalysts for this process stage are, for example, N,N-disubstituted carboxamides, such as DMF, N,N-dimethylacetamide or N,N-diisopropylacetamide. The catalyst is advantageously used in an amount of from 0.2 to 2 percent by weight, based on the acid chloride.

In the reaction with the acid chloride, heating is advantageously carried out until no further gas evolution occurs. It is advisable to remove excess acid chloride, for example by blowing in an inert gas, such as nitrogen, or by applying reduced pressure.

The potassium fluoride, which was advantageously dried beforehand, is then added to this mixture, and the mixture obtained by stirring is kept at the reaction temperature for from 1 to 10 hours.

According to the invention, suitable fluoride salts in addition to potassium fluoride are tetra-$C_1$-$C_{13}$-alkylammonium fluoride and corresponding mixtures with one another or with cesium fluoride or rubidium fluoride, these mixtures with cesium fluoride containing not more than 50% by weight of the latter. Preferably used fluoride mixtures are those which contain at least 75% by weight of potassium fluoride; in particular, such mixtures consist of at least 90% by weight of potassium fluoride and not more than 10% by weight of cesium fluoride or of 60% by weight of potassium fluoride and 40% by weight of rubidium fluoride. In a further preferred embodiment, only potassium fluoride is used as the fluoride salt.

Quaternary ammonium or phosphonium salts may be used as phase transfer catalysts. Examples of suitable compounds are tetra-$C_1$-$C_{18}$-alkylammonium chlorides, bromides or fluorides, tetra-$C_1$-$C_{18}$-alkylphosphonium chlorides or bromides, tetraphenylphosphonium chloride or bromide and (phenyl)$_m$($C_1$-$C_{18}$-alkyl)$_n$-phosphonium chlorides or bromides, where m is from 1 to 3, n is from 3 to 1 and m+n is 4. Mixtures of these salts may also be used. With a suitable choice of the catalyst for the particular compound to be reacted, which can readily be determined by a few routine experiments, the space-time yields and yields obtained are substantially better than those obtained by the process described in European Laid-open Application 146 924; moreover, the dead times of the apparatus and the total costs of the apparatus according to the novel process are substantially more advantageous.

The amount of phase transfer catalyst is in general up to 20, preferably from 3 to 15, particularly preferably from 3 to 8, % by weight, based on the amount of fluoride salt used.

Oligo- or polyalkylene glycol dimethyl ethers where the alkylene radical contains 2 to 6, preferably 2 and/or 3, carbon atoms, ie. is preferably the ethylene and/or the propylene radical and in particular only the ethylene radical, can also be used as phase transfer catalysts. The number of O-ethylene (glycol) units (—O—$CH_2$—$CH_2$—) and/or of O-propylene units in these compounds may be from n=4 (eg. tetraethylene glycol dimethyl ether) to about n=150; however, preferably used ethers are those whose degree of polymerization is from n=4 to n=25. In the case of alkylene radicals having more than 3 carbon atoms, n is in general no higher than 6. The amount of these ethers used, in particular glycol ethers, is in general from about 0.5 to about 200, preferably from about 5 to about 100, particularly preferably from about 10 to about 50, % by weight, based on the amount of fluoride salt used. The particular advantage of using these compounds is that in general, depending on the amount used, a smaller amount of solvent may be employed gince the glycol other is in general liquid at the reaction temperature. Mixtures of these ethers with one another as well as mixtures of these ethers (individually or as a mixture) with the quaternary ammonium or phosphonium salts, preferably glycol ethers with quaternary phosphonium salts, may also be used.

If tetra-$C_1$-$C_{18}$-alkylammonium fluorides are used as the fluoride salt, it is not necessary to add a further phase transfer catalyst since the fluoride salt itself is such a catalyst which can therefore be used in stoichiometric and larger amounts.

The use of spray-dried alkali metal fluoride in the novel process reduces the reaction times in some cases but is not absolutely essential. It is also possible to add acid acceptors, such as alkali metal and alkaline earth metal carbonates or basic oxides, for example magnesium oxide, or corresponding mixtures. Potassium carbonate is particularly preferred here and is used in amounts of from about 1 to about 10, preferably from about 4 to about 6, % by weight, based on the amount of fluoride salt.

The acid acceptors are in general not essential for the reaction. In some cases, the reaction rate is considerably reduced by the formation of hydrogen fluoride during the reaction. In these cases, it is advantageous to carry out the reaction in the presence of such acid acceptors, in particular to avoid corrosion of the apparatus. For reasons relating to corrosion in the fractionation unit, it may be desirable to use these compounds during fractionation of the reaction mixture or of the crude product, magnesium oxide being particularly preferred here. For this purpose, up to about 10, preferably from about 3 to 8, % by weight, based on the total amount of liquid used in the distillation, of acid acceptor are added to the fractionation still.

After the reaction with alkali metal fluoride, the mixture is worked up in a conventional manner, for example by filtration, washing of the solid material and distillation of filtrate and wash filtrates. In the case of water-miscible solvents, the pyridine derivatives Ia can also be precipitated by adding water and can be worked up in the manner described.

The process for the preparation of the compounds IIa in which at least one of the radicals $R^2$ to $R^4$ is fluorine comprises halogen exchange of a pyridinedicarboxylic anhydride IIb with potassium fluoride and is carried out in the same manner as the reaction of the pyridine derivatives Ib which is described above.

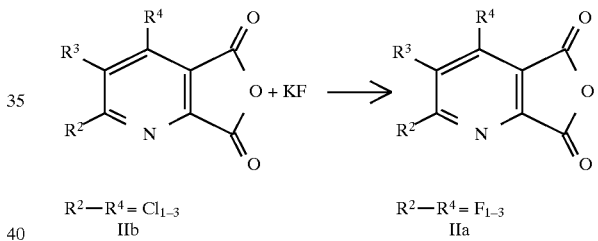

$R^2$—$R^4$ = $Cl_{1-3}$  $\qquad$  $R^2$—$R^4$ = $F_{1-3}$
IIb $\qquad\qquad\qquad\qquad$ IIa Instead of being effected at the stage of the pyridinedicarboxylic anhydrides IIb, the halogen exchange may also be carried out at the corresponding diester stage Vb. These can subsequently either be converted into the anhydrides IIa by hydrolysis and cyclization or reacted directly with the amine III to give carboxylic ester hemiamides VI, which can be hydrolyzed to give IV and then cyclized to give the novel compounds Ia.

Accordingly, a process for the preparation of pyridinedicarboxylates of the formula Va

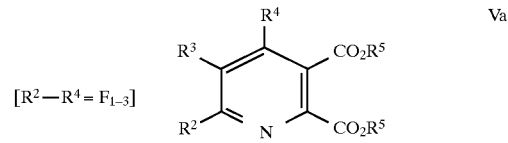

where $R^2$ to $R^4$ have the abovementioned meanings, at least one of the radicals $R^2$ to $R^4$ being fluorine and $R^5$ being an unsubstituted or substituted alkyl, alkenyl or alkynyl radical, for example halo-$C_1$-$C_4$-alkyl, halo-$C_3$-$C_5$-alkenyl, halo-$C_3$-$C_5$-alkynyl, $C_1$-$C_4$-alkoxy-$C_1$-$C_4$-alkyl, $C_1$-$C_4$-alkoxy-$C_3$-$C_5$-alKenyl, $C_1$-$C_4$-alkoxy-$C_3$-$C_5$-alkynyl, phenyl-$C_l$-$C_4$-alkyl, phenyl-$C_3$-$C_5$-alkanyl or phenyl-$C_3$-$C_5$-alkynyl, comprises subjecting a pyridinedicarboxylate of the formula Vb

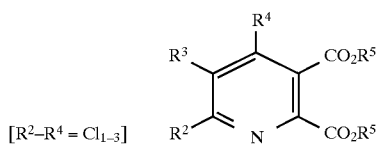

where $R^2$ to $R^5$ have the abovementioned meanings, at least one of the radicals $R^2$ to $R^4$ being chlorine, to halogen exchange with potasaium fluoride.

The process is carried out in the same manner as the reaction of the pyridine derivatives Ib which is described above. This is followed by the abovementioned conversions to the pyridine derivatives Ia.

one of the abovementioned inert solvents is initially taken, a tertiary base is added and the alkoxyacrolein VII is then introduced.

The tertiary base is generally added at from 60° to 120° C., preferably from 70° to 90° C.

The alkoxyacrolein VII is generally added at from 80° to 160° C., preferably from 110° to 130° C.

The molar ratios in which the acrolein VII and the dialkyl 2-amino-3-chloromaleate VIII are reacted with one another are from 0.9:1 to 1.5:1, preferably from 1:1 to 1.1:1.

The tertiary base is used in a ratio of from 0.9:1 to 1.5:1, preferably 1.1:1, based on the diester VIII of the maleic acid. The concentration of the starting materials in the solvent is from 0.1 to 5, preferably from 0.3 to 2, mol/l.

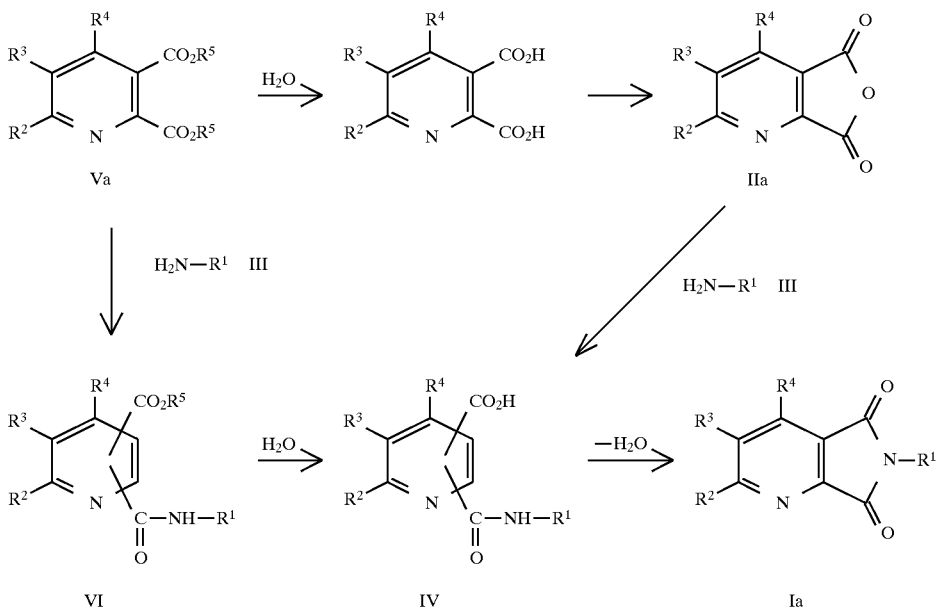

The molar ratios and the procedure are based on the reaction conditions for the preparation of IV or Ia or the process can be carried out in the individual steps according to general methods known trom the literature.

In the course of the preparation of the novel compounds, it was furthermore found that 5-alkoxypyridine-2,3-dicarboxylates of the formula Va''', where $R^3$ is $C_1-C_3$-alkoxy and $R^2$ and $R^4$ are each hydrogen, are advantageously obtained if an alkoxyacrolein VII is subjected to a condensation reaction with a dialkyl 2-amino-3-chloromaleate VIII.

Suitable aliphatic carboxylic acids are formic acid, acetic acid, propionic acid, butyric acid and isobutyric acid.

The tertiary bases used may be amines, such as triethylamine, tripropylamine or tributylamine, and aromatic bases, such as pyridine, α-, β- or γ-picoline, 2,4- and 2,6-lutidine or quinoline, and N,N-dialkylanilines, such as N,N-dimethyl- or N,N-diethylaniline.

The mixture can be worked up in a conventional manner, for example by evaporating down under reduced pressure, thoroughly washing the residue in water and filtering off or

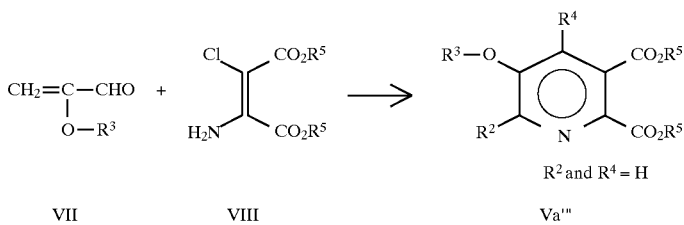

For this purpose, the dialkyl 2-amino-3-chloromaleate VIII in a lower aliphatic carboxylic acid and, if required, in extracting the product in an organic solvent and evaporating this solvent, similarly to the process described in EP 371 499.

Compared with the prior art, the novel fluorine-substituted pyridine-2,3-dicarboxylic anhydrides, esters and imides are obtainable in high yields in a particularly simple manner. Fluorine-substituted diesters are unknown to date. In the series comprising the anhydrides, preparation methods for the 5-fluoro- and the 4,5,6-trifluoropyridine derivatives were described in J. Org. Chem. 26 (1961) 808, and J. Fluorine Chem. 7 (1976), 363. In both methods, fluorine-substituted quinolines must first be synthesized in an inconvenient manner and then destroyed again by oxidation. The yield of the 5-fluoropyridine-2,3-dicarboxylic acid obtained by electrochemical oxidation is only 26% and, in the case of oxidation of the heptafluoroquinoline using nitric acid, only 5% of 4,5,6-trifluoropyridine-2,3-dicarboxylic anhydride are obtained (isolated as anhydride), in addition to 20% of 2,3,4,6,7-pentafluoro-5,8-dioxo-5,8-dihydroquinoline and 12% of 3,4,5,6,7,8-hexafluoro-2-oxo-1,2-dihydroquinoline.

In view of the intended use of the compounds I, suitable substituents are, for example, the following radicals:

$R^1$ is hydrogen;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy, ethoxy, 1-methylethoxy or 1,1-dimethylethoxy;

$C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimothylpropyl, 1-ethyl-1-methylpropyl or 1-ethyl-2-methylpropyl, in particular propyl, 1-methylethyl or 1,1-dimethylethyl, where the stated radicals may carry from one to three of the following groups:

$C_1$–$C_4$-alkoxy as stated above, in particular methoxy or ethoxy;

$C_1$–$C_4$-haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy or pentafluoroethoxy;

$C_1$–$C_4$-alkylthio, such as methylthio, ethylthio, propylthio, 1-methylethylthio, n-butylthio, 1-methylpropylthio, 2-methylpropylthio and 1,1-dimethylethylthio, in particular methylthio or ethylthio;

$C_1$–$C_4$-haloalkylthio, such as difluoromethylthio, tritluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio or pentafluoroethylthio, in particular trifluoromethylthio or pentafluoroethylthio;

$C_1$–$C_4$-dialkylamino, such as dimethylamino, diethylamino, dipropylamino, diisopropylamino, dibutylamino or mothylethylamino, in particular dimethylamino or methylethylamino;

$C_3$–$C_8$-cycloalkyl, such as cyclopropyl, cyclobutyl, cyclopentyl, cyclohexyl, cycloheptyl or cyclooctyl, in particular cyclopropyl, cyclopentyl or cyclohexyl;

halogen, such as fluorine, chlorine, bromine or iodine, in particular fluorine or chlorine;

$R^1$ may furthermore be $C_3$–$C_8$-cycloalkyl as stated above, in particular cyclopropyl, cyclobutyl, cyclopentyl or cyclohexyl, which may carry from one to three of the following groups: $C_1$–$C_6$-alkyl as stated above, in particular methyl, ethyl or isopropyl; haloalkyl as stated above for the homologous haloalkylthio radicals, in particular trifluoromethyl; $C_1$–$C_4$-alkoxy as stated above, in particular methoxy or ethoxy; $C_1$–$C_4$-haloalkoxy as stated above, in particular trifluoromethoxy; halogen as stated above, in particular fluorine or chlorine;

$C_3$–$C_6$-alkenyl, such as 2-propenyl, 2-methylethenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 1-, 2-, 3-, 4- or 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4 vethyl-3-pentenyl, 1-methyl-4-pentenyl, 2-methyl-4-pentenyl, 3-methyl-4-pentenyl, 4-methyl-4-pentenyl, 1,1-dimethyl-2-butenyll 1,1-dimethyl-3-butenyl, 1,2-dimethyl-2-butenyl, 1,2-dimethyl-3-butenyl, 1,3-dimethyl-2-butenyl, 1,3-di-methyl-3-butenyl, 2,2-dimethyl-3-butenyl, 2,3-dimethyl-2-butenyl, 2,3-dimethyl-3-butenyl, 1-ethyl-2-butenyl, 1-athyl-3-butenyl, 2-ethyl-2-butenyl, 2-ethyl-3-butenyl, 1,1,2-trimethyl-2-propanyl, 1-ethyl-1-methyl-2-pentenyl or ethyl-2-methyl-2-pentenyl, in particular ethenyl, 2-propenyl, 1-methylethenyl, 2-butenyl, 3-butenyl, 1-methylpropyl, 1-methyl-2-propenyl or 2-methyl-2-propenyl, which may be monosubmtituted to trisubstituted by halogen, in particular by fluorine or chlorine;

$R^1$ may furthermore be $C_3$–$C_6$-alkynyl, such as propargyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 3-methyl-1-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, in particular 1-methyl-2-propynyl or 1,1-dimethyl-2-propynyl, which may be monosubstituted to trisubstituted by halogen as stated above, in particular fluorine or chlorine, and/or monosubstituted by phenyl;

$R^2$, $R^3$ and $R^4$ are each hydrogen, halogen as stated under $R^1$, in particular fluorine or chlorine; cyano; $C_1$–$C^6$-alkyl as stated under $R^1$, in particular methyl, ethyl, propyl, 1-methylethyl or 1,1-dimethylethyl, which may carry from one to five halogen atoms as stated under $R^1$, in particular fluorine or chlorine, and/or one or two of the following radicals: $C_1$–$C_4$-alkoxy as stated under $R^1$, in particular methoxy, ethoxy, 1-methylethoxy or 1,1-dimethylethoxy; $C_1$–$C_4$-haloalkoxy as stated under R$^1$, in particular halomethoxy, such as difluoromethoxy or trifluoromethoxy; C$_1$–C$_4$-alkylthio as stated under R$^1$, in particular methylthio or ethylthio; C$_1$–C$_4$-haloalkylthio as stated under R$^1$, in particular difluoromethylthio or trifluoromethylthio;

C$_3$–C$_6$-cycloalkyl as stated under R$^1$, in particular cyclopropyl;

R$^2$, R$^3$ and R$^4$ may each furthermore be benzyl which may be monosubstituted to trisubstituted by C$_1$–C$_4$-alkyl as stated under R$^1$, in particular methyl, ethyl or 1-ethylethyl, by C$_1$–C$_4$-haloalkyl as stated under R$^1$, in particular trifluoromethyl or chlorodifluoromethyl, by C$_1$–C$_4$-alkoxy as stated under R$^1$, in particular methoxy or ethoxy; by C$_1$–C$_4$-haloalkoxy as stated under R$^1$, in particular trifluoromethoxy, trichloromethoxy or pentafluoroethoxy, by C$_1$–C$_4$-alkylthio as stated under R$^1$, in particular methylthio or ethylthio, by C$_1$–C$_4$-haloalkylthio as stated under R$^1$, in particular difluoromethylthio, trifluoromethylthio or pentafluoromethylthio, by halogen, in particular fluorine or chlorine, by cyano or by nitro;

R$^2$, R$^3$ and R$^4$ may furthermore each be C$_3$–C$_8$-cycloalkyl as stated under R$^1$, in particular cyclopropyl, cyclopentyl or cyclohexyl, which may be monosubstituted to trisubstituted by C$_1$–C$_4$-alkyl as stated under R$^1$, in particular methyl or ethyl, or by halogen as stated under R$^1$, in particular fluorine or chlorine;

C$_2$–C$_6$-alkenyl as stated under R$^1$, and 1-ethenyl, 1-propenyl, 1-methyl-1-propenyl, 2-methyl-1-propenyl, 1-pentenyl, 1-methyl-1-butenyl, 2-methyl-1-butenyl, 1-ethyl-1-propenyl, 1-methyl-1-pentenyl, 2-methyl-1-pentenyl, 3-methyl-1-pentenyl, 4-methyl-1-pentenyl, 1,2-dimethyl-1-butenyl, 1,3-dimethyl-1-butenyl, 2,3-dimethyl-1-butenyl, 3,3-dimethyl-1-butenyl, ethyl-1-butenyl, 2-ethyl-1-butenyl or 1-ethyl-2-methyl-1-pentenyl, in particular ethenyl, 1-propenyl, 2-propenyl, 1-methylethenyl, 1-butenyl, 2-butenyl, 3-butenyl, 1-methylpropenyl, 1-methyl-2-propenyl, 2-methyl-1-propenyl or 2-methyl-2-propenyl, which may be monosubstituted to trisubstituted by halogen as stated under R$^1$, in particular fluorine or chlorine, or by C$_1$–C$_3$-alkoxy as stated under R$^1$, in particular methoxy or ethoxy, and/or mono-substituted by phenyl, where the phenyl radical in turn may carry from one to three of the following groups: alkyl as stated under R$^1$, in particular methyl, ethyl or 1-methylethyl; haloalkyl as stated under R$^1$, in particular trifluoromethyl or chlorodifluoromethyl, alkoxy as stated under R$^1$, in particular methoxy or ethoxy, haloalkoxy as stated under R$^1$, in particular trifluoromethoxy, trichloromethoxy or pentafluoroethoxy, alkylthio as stated under R$^1$, in particular methylthio or ethylthio, haloalkylthio as stated under R$^1$, in particular difluoromethylthio, trifluoromethylthio or pentafluoromethylthio, halogen as stated under R$^1$, in particular fluorine or chlorine, cyano or nitro;

C$_2$–C$_6$-alkynyl as stated under R$^1$, and ethynyl, 1-propynyl, 1-butynyl, 1-pentynyl, 1-hexynyl, 3-methyl-1-pentynyl or 4-methyl-1-pentynyl, in particular ethynyl, 1-propynyl or propargyl, which may be monosubstituted to trisubstituted by halogen as stated above, in particular fluorine or chlorine, or by alkoxy as stated above, in particular methoxy or ethoxy, and/or monosubstituted by phenyl, where the phenyl radical in turn may carry from one to three of the following groups: alkyl as stated above, in particular methyl, ethyl or 1-methylethyl, haloalkyl as stated above, in particular trifluoromethyl or chlorodifluoromethyl, alkoxy as stated above, in particular methoxy or ethoxy, haloalkoxy as stated above, in particular trifluoromethoxy, trichloromethoxy or pentafluoroethoxy, alkylthio as stated above, in particular methylthio or ethylthio, haloalkylthio as stated above, in particular difluoromethylthio, trifluoromethylthio or pentafluoromethylthio, halogen as stated above, in particular fluorine or chlorine, cyano or nitro;

R$^2$, R$^3$ and R$^4$ may furthermore be C$_1$–C$_4$-alkoxy or C$_1$–C$_4$-alkylthio as stated under R$^1$, in particular methoxy or othoxy and methylthio or ethylthio;

C$_1$–C$_4$-haloalkoxy or C$_1$–C$_4$-haloalkylthio as stated above, in particular trifluoromethoxy, trichloromethoxy or pentafluoroethoxy and difluoromethylthio, trifluoromethylthio or pentafluoroethylthio;

C$_2$–C$_5$-alkenyloxy, such as vinyloxy, 2-propenyloxy, 1-methylethenyloxy or 2-methyl-3-butenyloxy, in particular 2-propenyloxy or 2-methyl-3-butenyloxy;

C$_2$–C$_5$-alkynyloxy, such as ethynyloxy, 2-propynyloxy, 1-methylethynyloxy or 2-methyl-3-butynyloxy, in particular 2-propynyloxy or 2-methyl-3-butynyloxy;

C$_1$–C$_4$-alkylsulfinyl, such as methylsulfinyl, ethylsulfinyl, n-propylsulfinyl, isopropylsulfinyl, n-butylsulfinyl or tertbutylsulfinyl, in particular methylsulfinyl;

C$_1$–C$_4$-alkylsulfonyl, such as methylsulfonyl, ethylsulfonyl, n-propylsulfonyl, isopropylsulfonyl, n-butylsulfonyl or tert-butylsulfonyl, in particular methylsulfonyl;

C$_1$–C$_4$-haloalkylsulfonyl, such as trifluoromethylsulfonyl, pentafluoroethylsulfonyl or monofluorobutylsulfonyl, in particular trifluoromethylsulfonyl;

phenoxy or phenylthio which may be monosubstituted to trisubstituted by C$_1$–C$_4$-alkyl as stated under R$^1$, in particular methyl, ethyl or isopropyl, by haloalkyl as stated under R$^1$, in particular trifluoromethyl or chlorodifluoromethyl, by alkoxy as stated above, in particular methoxy or ethoxy, by haloalkoxy as stated above, in particular trifluoromethoxy, trichloromethoxy or pentafluoroethoxy, by alkylthio as stated above, in particular methylthio or ethylthio, by haloalkylthio as stated above, in particular difluoromethylthio, trifluoromethylthio or pentafluoromethylthio, by halogen as stated above, in particular fluorine or chlorine, by cyano or by nitro;

a 5-membered or 6-membered saturated or aromatic heterocyclic radical containing one or two hetero atoms selected from the group consisting of oxygen, sulfur and nitrogen, such as tetrahydrofuryl, tetrahydropyranyl, furyl, thienyl, thiazolyl, pyrazolyl, pyrrolyl, pyridyl, morpholino, piperidino or pyrimidyl, for example 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furyl, 3-furyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl or 4-pyridyl, which may carry from one to three of the following substituents: C$_1$–C$_3$-alkyl as stated above, in particular methyl or ethyl, halogen as stated above, in particular fluorine or chlorine, $C_2$–$C_3$-alkoxy as stated under $R^1$, in particular methoxy or ethoxy, or $C_2$–$C_4$-alkoxycarbonyl, such as methoxycarbonyl or ethoxycarbonyl, in particular methoxycarbonyl;

phenyl which may carry from one to three of the following groups: $C_1$–$C_6$-alkyl as stated under $R^1$, in particular methyl, ethyl or isopropyl; $C_1$–$C_6$-haloalkyl as stated under $R^1$, in particular trifluoromethyl or chlorodifluoromethyl; $C_1$–$C_6$-alkoxy as stated under $R^1$, in particular methoxy or ethoxy; $C_1$–$C_6$-haloalkoxy as stated under $R^1$, in particular trifluoromethoxy, trichloromethoxy or pentafluoroethoxy; $C_1$–$C_6$-alkylthio as stated under $R^1$, in particular methylthio or ethylthio; $C_1$–$C_6$-haloalkylthio as stated under $R^1$, in particular difluoromethylthio, trifluoromethylthio or pentafluoromethylthio; halogen as stated under $R^1$, in particular fluorine or chlorine; cyano or nitro; with the proviso that one of the three substituents $R^1$, $R^3$ and $R^4$ is defined as stated at the outset.

Examples of preferred combinations of radicals in the pyridine ring are shown in the table below, $R^1$ corresponding to a radical from the groups L1 to L64, in particular 1-cyclopropylethyl or cyclopropyl.

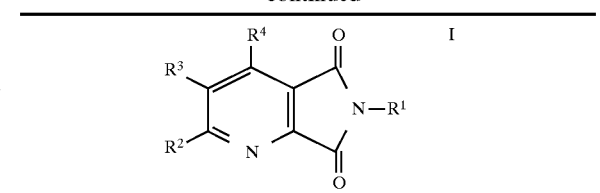

| $R^2$ | $R^3$ | $R^4$ |
|---|---|---|
| F | H | H |
| F | F | H |
| F | H | F |
| F | F | F |
| F | Cl | H |
| F | H | Cl |
| F | Cl | Cl |
| F | F | Cl |
| F | Cl | F |
| F | CN | H |
| F | H | CN |
| F | CN | CN |
| F | CN | F |
| F | F | CN |
| F | Cl | CN |
| F | CN | Cl |
| F | $CH_3$ | H |
| F | H | $CH_3$ |
| F | $CH_3$ | $CH_3$ |
| F | F | $CH_3$ |
| F | $CH_3$ | F |
| F | $CH_3$ | Cl |
| F | Cl | $CH_3$ |
| F | $C_2H_5$ | F |
| F | F | $C_2H_5$ |
| F | $CF_3$ | H |
| F | H | $CF_3$ |
| F | Cl | $CF_3$ |
| F | $CF_3$ | Cl |
| F | $C_2F_5$ | H |
| F | H | $C_2F_5$ |
| F | $CH_2OCH_3$ | H |
| F | H | $CH_2OCH_3$ |
| F | $CH_2OCH_3$ | F |
| F | $CH_2SCH_3$ | H |
| F | H | $CH_2SCH_3$ |
| F | $CH_2SCH_3$ | Cl |
| F | Cl | $CH_2SCH_3$ |
| F | $CH_2$-cyclopropyl | H |
| F | 1-(cyclopropyl)ethyl | H |

-continued

| $R^2$ | $R^3$ | $R^4$ |
|---|---|---|
| F | $CH_2CN$ | H |
| F | H | $CH_2CN$ |
| F | $CH_3$ | $CH_2CN$ |
| F | benzyl | F |
| F | Cl | benzyl |
| F | benzyl | F |
| F | F | benzyl |
| F | 4-chlorobenzyl | H |
| F | 3-$CF_3$-benzyl | H |
| F | 2,4-$Cl_2$-benzyl | H |
| F | 3-$OCH_3$-phenyl | H |
| F | H | 3-$OCH_3$-benzyl |
| F | 3-CN-benzyl | H |
| F | cyclopropyl | H |
| F | cyclopropyl | Cl |
| F | cyclopropyl | F |
| F | $CH{=}CH_2$ | H |
| F | F | $CH{=}CH_2$ |
| F | $CF{=}CF_2$ | H |
| F | $CH_3$ | $CF{=}CF_2$ |
| F | $CH_3$ | benzyl |
| F | $CH{=}CH{-}OCH_3$ | H |
| F | $CH{=}CH{-}OCH_3$ | Cl |
| F | $CH{=}CH{-}OCH_3$ | F |
| F | $CH{=}CH$-phenyl | H |
| F | $CH{=}CH$-phenyl | F |
| F | $CH{=}CH$-phenyl | Cl |
| F | $CH{=}CH$-(3-chlorophenyl) | H |
| F | $CH{=}CH$-(3-chlorophenyl) | F |
| F | $C{\equiv}CH$ | H |
| F | $CH_2{-}C{\equiv}CH$ | H |
| F | $CH_2{-}C{\equiv}CH$ | F |
| F | $CH_3O$ | H |
| F | $CH_3O$ | F |
| F | $CH_3O$ | Cl |
| F | $CH_3O$ | $CH_3$ |
| F | H | $CH_3O$ |
| F | Cl | $CH_3O$ |
| F | F | $CH_3O$ |
| F | $CH_3$ | $CH_3O$ |
| F | $CH_3O$ | $CH_3O$ |
| F | $CH_3S$ | H |
| F | $CH_3S$ | F |
| F | $CH_3S$ | Cl |
| F | $CH_3S$ | $CH_3$ |
| F | H | $CH_3S$ |
| F | F | $CH_3S$ |
| F | Cl | $CH_3S$ |
| F | $CH_3$ | $CH_3S$ |
| F | $CF_3O$ | H |
| F | $CF_3O$ | F |
| F | $CF_3O$ | Cl |
| F | $F_2CHO$ | H |
| F | $F_2CHO$ | F |
| F | $F_2CHO$ | Cl |
| F | $SCF_3$ | H |
| F | $SCF_3$ | F |
| F | $SCF_3$ | Cl |
| F | $CH_3SO$ | H |
| F | $CH_3SO$ | F |
| F | $CH_3SO$ | Cl |
| F | $CH_3SO_2$ | H |
| F | $CH_3SO_2$ | Cl |
| F | $CH_3SO_2$ | F |
| F | $CF_3SO_2$ | H |
| F | $CF_3SO_2$ | F |

-continued

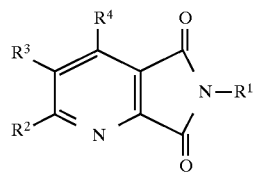

| R² | R³ | R⁴ |
|---|---|---|
| F | CF₃SO₂ | Cl |
| F | O-phenyl | H |
| F | O-phenyl | F |
| F | O-(4-Cl-phenyl) | H |
| F | O-(3-CF₃-phenyl) | H |
| F | O-(2,4-Cl₂-phenyl) | H |
| F | O-(4-CH₃O-phenyl) | H |
| F | O-(3-CN-phenyl) | H |
| F | S-phenyl | H |
| F | S-(3-Cl-phenyl) | H |
| F | 2-tetrahydrofuranyl | H |
| F | 3-tetrahydrofuranyl | H |
| F | 2-tetrahydrothienyl | H |
| F | 3-tetrahydrothienyl | H |
| F | 2-tetrahydropyranyl | H |
| F | 3-tetrahydropyranyl | H |
| F | 4-tetrahydropyranyl | H |
| F | 2-furyl | H |
| F | 3-furyl | H |
| F | 2-thienyl | H |
| F | 3-thienyl | H |
| F | 3-isoxazolyl | H |
| F | 4-isoxazolyl | H |
| F | 5-isoxazolyl | H |
| F | 3-isothiazolyl | H |
| F | 4-isothiazolyl | H |
| F | 5-isothiazolyl | H |
| F | 2-oxazolyl | H |
| F | 4-oxazolyl | H |
| F | 5-oxazolyl | H |
| F | 2-thiazolyl | H |
| F | 4-thiazolyl | H |
| F | 5-thiazolyl | H |
| F | 2-imidazolyl | H |
| F | 4-imidazolyl | H |
| F | 5-imidazolyl | H |
| F | 2-pyrrolyl | H |
| F | 3-pyrrolyl | H |
| F | 3-pyrazolyl | H |
| F | 4-pyrazolyl | H |
| F | 5-pyrazolyl | H |
| F | 2-pyridyl | H |
| F | 3-pyridyl | H |
| F | 4-pyridyl | H |
| F | phenyl | H |
| F | 4-Cl-phenyl | H |
| F | 2,4-Cl₂-phenyl | H |
| F | 3-CF₃-phenyl | H |
| F | 3-CH₃O-phenyl | H |
| H | Cl | F |
| H | Cl | Cl |
| H | Cl | CN |
| H | Cl | CH₃ |
| H | Cl | CH₃O |
| H | Cl | C₂H₅O |
| H | Cl | CH₃S |
| H | Cl | C₂H₅S |
| H | Cl | benzyl |
| H | Cl | CF=CF₂ |
| H | Cl | C₂F₅ |
| H | Cl | cyclopropyl |
| H | Cl | C₂H₅ |
| H | Cl | CF₃O |
| H | Cl | F₂CHO |
| H | Cl | C₂F₅O |
| H | Cl | CF₃S |
| H | Cl | F₂CHS |
| H | Cl | CF₃ |

-continued

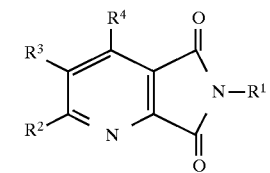

| R² | R³ | R⁴ |
|---|---|---|
| H | Cl | CH₃SO |
| H | Cl | CH₃SO₂ |
| H | Cl | CF₃SO₂ |
| H | Cl | O-phenyl |
| H | Cl | O-(4-Cl-phenyl) |
| H | F | O-(3-CF₃-phenyl) |
| H | F | H |
| H | F | F |
| H | F | Cl |
| H | F | CN |
| H | F | CH₃ |
| H | F | CH₃O |
| H | F | C₂H₅O |
| H | F | CH₃S |
| H | F | C₂H₅S |
| H | F | benzyl |
| H | F | CF=CF₂ |
| H | F | C₂F₅ |
| H | F | cyclopropyl |
| H | F | C₂H₅ |
| H | F | CF₃O |
| H | F | F₂CHO |
| H | F | C₂F₅O |
| H | F | CF₃S |
| H | F | F₂CHS |
| H | F | CF₃ |
| H | F | CH₃SO |
| H | F | CH₃SO₂ |
| H | F | CF₃SO₂ |
| H | F | O-phenyl |
| H | F | O-(4-Cl-phenyl) |
| H | CH₃O | O-(3-CF₃-phenyl) |
| H | CH₃O | H |
| H | CH₃O | F |
| H | CH₃O | Cl |
| H | CH₃O | CN |
| H | CH₃O | CH₃ |
| H | CH₃O | CH₃O |
| H | CH₃O | C₂H₅O |
| H | CH₃O | CH₃S |
| H | CH₃O | C₂H₅S |
| H | CH₃O | benzyl |
| H | CH₃O | CF=CF₂ |
| H | CH₃O | C₂F₅ |
| H | CH₃O | cyclopropyl |
| H | CH₃O | C₂H₅ |
| H | CH₃O | CF₃O |
| H | CH₃O | F₂CHO |
| H | CH₃O | C₂F₅O |
| H | CH₃O | CF₃S |
| H | CH₃O | F₂CHS |
| H | CH₃O | CF₃ |
| H | CH₃O | CH₃SO |
| H | CH₃O | CH₃SO₂ |
| H | CH₃O | CF₃SO₂ |
| H | CH₃O | O-phenyl |
| H | CH₃O | O-(4-Cl-phenyl) |
| H | Br | O-(3-CF₃-phenyl) |
| H | Br | H |
| H | Br | F |
| H | Br | Cl |
| H | Br | CN |
| H | Br | CH₃ |
| H | Br | CH₃O |
| H | Br | C₂H₅O |
| H | Br | CH₃S |
| H | Br | C₂H₅S |
| H | Br | benzyl |
| H | Br | CF=CF₂ |

21

-continued structure I: pyridine-dicarboximide with R³, R⁴ on ring and N—R¹

| R² | R³ | R⁴ |
|---|---|---|
| H | Br | C₂F₅ |
| H | Br | cyclopropyl |
| H | Br | C₂H₅ |
| H | Br | CF₃O |
| H | Br | F₂CHO |
| H | Br | C₂F₅O |
| H | Br | CF₃S |
| H | Br | F₂CHS |
| H | Br | CF₃ |
| H | Br | CH₃SO |
| H | Br | CH₃SO₂ |
| H | Br | CF₃SO₂ |
| H | Br | O-phenyl |
| H | Br | O-(4-Cl-phenyl) |
| H | CF₃ | O-(3-CF₃-phenyl) |
| H | CF₃ | H |
| H | CF₃ | F |
| H | CF₃ | Cl |
| H | CF₃ | CN |
| H | CF₃ | CH₃ |
| H | CF₃ | CH₃O |
| H | CF₃ | C₂H₅O |
| H | CF₃ | CH₃S |
| H | CF₃ | C₂H₅S |
| H | CF₃ | benzyl |
| H | CF₃ | CF=CF₂ |
| H | CF₃ | C₂F₅ |
| H | CF₃ | cyclopropyl |
| H | CF₃ | C₂H₅ |
| H | CF₃ | CF₃O |
| H | CF₃ | F₂CHO |
| H | CF₃ | C₂F₅O |
| H | CF₃ | CF₃S |
| H | CF₃ | F₂CHS |
| H | CF₃ | CF₃ |
| H | CF₃ | CH₃SO |
| H | CF₃ | CH₃SO₂ |
| H | CF₃ | CF₃SO₂ |
| H | CF₃ | O-phenyl |
| H | CF₃ | O-(4-Cl-phenyl) |
| H | CN | O-(3-CF₃-phenyl) |
| H | CN | H |
| H | CN | F |
| H | CN | Cl |
| H | CN | CN |
| H | CN | CH₃ |
| H | CN | CH₃O |
| H | CN | C₂H₅O |
| H | CN | CH₃S |
| H | CN | C₂H₅S |
| H | CN | benzyl |
| H | CN | CF=CF₂ |
| H | CN | C₂F₅ |
| H | CN | cyclopropyl |
| H | CN | C₂H₅ |
| H | CN | CF₃O |
| H | CN | F₂CHO |
| H | CN | C₂F₅O |
| H | CN | CF₃S |
| H | CN | F₂CHS |
| H | CN | CF₃ |
| H | CN | CH₃SO |
| H | CN | CH₃SO₂ |
| H | CN | CF₃SO₂ |
| H | CN | O-phenyl |
| H | CN | C-(4-Cl-phenyl) |
| H | CH₂CH=CH₂O | O-(3-CF₃-phenyl) |
| H | CH₂CH=CH₂O | H |
| H | CH₂CH=CH₂O | F |

22

-continued

| R² | R³ | R⁴ |
|---|---|---|
| H | CH₂CH=CH₂O | Cl |
| H | CH₂CH=CH₂O | CN |
| H | CH₂CH=CH₂O | CH₃ |
| H | CH₂CH=CH₂O | CH₃O |
| H | CH₂CH=CH₂O | C₂H₅O |
| H | CH₂CH=CH₂O | CH₃S |
| H | CH₂CH=CH₂O | C₂H₅S |
| H | CH₂CH=CH₂O | benzyl |
| H | CH₂CH=CH₂O | CF=CF₂ |
| H | CH₂CH=CH₂O | C₂F₅ |
| H | CH₂CH=CH₂O | cyclopropyl |
| H | CH₂CH=CH₂O | C₂H₅ |
| H | CH₂CH=CH₂O | CF₃O |
| H | CH₂CH=CH₂O | F₂CHO |
| H | CH₂CH=CH₂O | C₂F₅O |
| H | CH₂CH=CH₂O | CF₃S |
| H | CH₂CH=CH₂O | F₂CHS |
| H | CH₂CH=CH₂O | CF₃ |
| H | CH₂CH=CH₂O | CH₃SO |
| H | CH₂CH=CH₂O | CH₃SO₂ |
| H | CH₂CH=CH₂O | CF₃SO₂ |
| H | CH₂CH=CH₂O | O-phenyl |
| H | CH₂CH=CH₂O | O-(4-Cl-phenyl) |
| H | HC≡C—CH₂O | O-(3-CF₃-phenyl) |
| H | HC≡C—CH₂O | H |
| H | HC≡C—CH₂O | F |
| H | HC≡C—CH₂O | Cl |
| H | HC≡C—CH₂O | CN |
| H | HC≡C—CH₂O | CH₃ |
| H | HC≡C—CH₂O | CH₃O |
| H | HC≡C—CH₂O | C₂H₅O |
| H | HC≡C—CH₂O | CH₃S |
| H | HC≡C—CH₂O | C₂H₅S |
| H | HC≡C—CH₂O | benzyl |
| H | HC≡C—CH₂O | CF=CF₂ |
| H | HC≡C—CH₂O | C₂F₅ |
| H | HC≡C—CH₂O | cyclopropyl |
| H | HC≡C—CH₂O | C₂H₅ |
| H | HC≡C—CH₂O | CF₃O |
| H | HC≡C—CH₂O | F₂CHO |
| H | HC≡C—CH₂O | C₂F₅O |
| H | HC≡C—CH₂O | CF₃S |
| H | HC≡C—CH₂O | F₂CHS |
| H | HC≡C—CH₂O | CF₃ |
| H | HC≡C—CH₂O | CH₃SO |
| H | HC≡C—CH₂O | CH₃SO₂ |
| H | HC≡C—CH₂O | CF₃SO₂ |
| H | HC≡C—CH₂O | O-phenyl |

-continued

| R² | R³ | R⁴ |
|---|---|---|
| H | HC≡C—CH₂O | O-(4-Cl-phenyl) |
| F | Cl | Et |
| F | Cl | CF₃O |
| F | Cl | F₂CHO |
| F | Cl | C₂F₅O |
| F | Cl | CF₃S |
| F | Cl | F₂CHS |
| F | Cl | CH₃SO |
| F | Cl | CH₃SO₂ |
| F | Cl | CF₃SO₂ |
| F | Cl | O-phenyl |
| F | Cl | O-(4-Cl-phenyl) |
| F | Cl | ClCF₂O |
| F | Cl | i-C₃H₇ |
| F | Cl | i-C₄H₉ |
| Cl | Cl | O-(3-CF₃-phenyl) |
| Cl | Cl | H |
| Cl | Cl | F |
| Cl | Cl | Cl |
| Cl | Cl | CN |
| Cl | Cl | CH₃ |
| Cl | Cl | CH₃O |
| Cl | Cl | C₂H₅O |
| Cl | Cl | CH₃S |
| Cl | Cl | C₂H₅S |
| Cl | Cl | benzyl |
| Cl | Cl | CF=CF₂ |
| Cl | Cl | C₂F₅ |
| Cl | Cl | cyclopropyl |
| Cl | Cl | C₂H₅ |
| Cl | Cl | CF₃O |
| Cl | Cl | F₂CHO |
| Cl | Cl | C₂F₅O |
| Cl | Cl | CF₃S |
| Cl | Cl | F₂CHS |
| Cl | Cl | CF₃ |
| Cl | Cl | CH₃SO |
| Cl | Cl | CH₃SO₂ |
| Cl | Cl | CF₃SO₂ |
| Cl | Cl | O-phenyl |
| Cl | Cl | O-(4-Cl-phenyl) |
| CH₃O | Cl | O-(3-CF₃-phenyl) |
| CH₃O | Cl | H |
| CH₃O | Cl | F |
| CH₃O | Cl | Cl |
| CH₃O | Cl | CN |
| CH₃O | Cl | CH₃ |
| CH₃O | Cl | CH₃O |
| CH₃O | Cl | C₂H₅O |
| CH₃O | Cl | CH₃S |
| CH₃O | Cl | C₂H₅S |
| CH₃O | Cl | benzyl |
| CH₃O | Cl | CF=CF₂ |
| CH₃O | Cl | C₂F₅ |
| CH₃O | Cl | cyclopropyl |
| CH₃O | Cl | C₂H₅ |
| CH₃O | Cl | CF₃O |
| CH₃O | Cl | F₂CHO |
| CH₃O | Cl | C₂F₅O |
| CH₃O | Cl | CF₃S |
| CH₃O | Cl | F₂CHS |
| CH₃O | Cl | CF₃ |
| CH₃O | Cl | CH₃SO |
| CH₃O | Cl | CH₃SO₂ |
| CH₃O | Cl | CF₃SO₂ |
| CH₃O | Cl | O-phenyl |
| CH₃O | Cl | O-(4-Cl-phenyl) |
| CH₃ | Cl | O-(3-CF₃-phenyl) |
| CH₃ | Cl | H |
| CH₃ | Cl | F |
| CH₃ | Cl | Cl |
| CH₃ | Cl | CN |
| CH₃ | Cl | CH₃ |
| CH₃ | Cl | CH₃O |
| CH₃ | Cl | C₂H₅O |
| CH₃ | Cl | CH₃S |
| CH₃ | Cl | C₂H₅S |
| CH₃ | Cl | benzyl |
| CH₃ | Cl | CF=CF₂ |
| CH₃ | Cl | C₂F₅ |
| CH₃ | Cl | cyclopropyl |
| CH₃ | Cl | C₂H₅ |
| CH₃ | Cl | CF₃O |
| CH₃ | Cl | F₂CHO |
| CH₃ | Cl | C₂F₅O |
| CH₃ | Cl | CF₃S |
| CH₃ | Cl | F₂CHS |
| CH₃ | Cl | CF₃ |
| CH₃ | Cl | CH₃SO |
| CH₃ | Cl | CH₃SO₂ |
| CH₃ | Cl | CF₃SO₂ |
| CH₃ | Cl | O-phenyl |
| CH₃ | Cl | O-(4-Cl-phenyl) |
| F | CH₃ | C₂H₅ |
| F | CH₃ | CF₃O |
| F | CH₃ | F₂CHO |
| F | CH₃ | C₂H₅O |
| F | CH₃ | CF₃S |
| F | CH₃ | CH₃SO |
| F | CH₃ | CH₃SO₂ |
| F | CH₃ | CF₃SO₂ |
| F | CH₃ | O-phenyl |
| F | CH₃ | O-(4-Cl-phenyl) |
| F | CH₃ | ClCF₂O |
| F | CH₃ | i-C₃H₇ |
| F | CH₃ | CN |
| Cl | CH₃O | O-(3-CF₃-phenyl) |
| Cl | CH₃O | H |
| Cl | CH₃O | F |
| Cl | CH₃O | Cl |
| Cl | CH₃O | CN |
| Cl | CH₃O | CH₃ |
| Cl | CH₃O | CH₃O |
| Cl | CH₃O | C₂H₅O |
| Cl | CH₃O | CH₃S |
| Cl | CH₃O | C₂H₅S |
| Cl | CH₃O | benzyl |
| Cl | CH₃O | CF=CF₂ |
| Cl | CH₃O | C₂F₅ |
| Cl | CH₃O | cyclopropyl |
| Cl | CH₃O | C₂H₅ |
| Cl | CH₃O | CF₃O |
| Cl | CH₃O | F₂CHO |
| Cl | CH₃O | C₂F₅O |
| Cl | CH₃O | CF₃S |
| Cl | CH₃O | F₂CHS |
| Cl | CH₃O | CF₃ |
| Cl | CH₃O | CH₃SO |
| Cl | CH₃O | CH₃SO₂ |
| Cl | CH₃O | CF₃SO₂ |
| Cl | CH₃O | O-phenyl |
| Cl | CH₃O | O-(4-Cl-phenyl) |
| Cl | CF₃ | O-(3-CF₃-phenyl) |
| Cl | CF₃ | H |
| Cl | CF₃ | F |
| Cl | CF₃ | Cl |
| Cl | CF₃ | CN |

I (Structure: pyridine ring with R³, R⁴, R² substituents and an imide group N–R¹ with two C=O)

| R² | R³ | R⁴ |
|---|---|---|
| Cl | CF₃ | CH₃ |
| Cl | CF₃ | CH₃O |
| Cl | CF₃ | C₂H₅O |
| Cl | CF₃ | CH₃S |
| Cl | CF₃ | C₂H₅S |
| Cl | CF₃ | benzyl |
| Cl | CF₃ | CF=CF₂ |
| Cl | CF₃ | C₂F₅ |
| Cl | CF₃ | cyclopropyl |
| Cl | CF₃ | C₂H₅ |
| Cl | CF₃ | CF₃O |
| Cl | CF₃ | F₂CHO |
| Cl | CF₃ | C₂F₅O |
| Cl | CF₃ | CF₃S |
| Cl | CF₃ | F₂CHS |
| Cl | CF₃ | CF₃ |
| Cl | CF₃ | CH₃SO |
| Cl | CF₃ | CH₃SO₂ |
| Cl | CF₃ | CF₃SO₂ |
| Cl | CF₃ | O-phenyl |
| Cl | CF₃ | O-(4-Cl-phenyl) |
| Cl | CF₃ | O-(3-CF₃-phenyl) |
| CH₃ | CH₃O | H |
| CH₃ | CH₃O | F |
| CH₃ | CH₃O | Cl |
| CH₃ | CH₃O | CN |
| CH₃ | CH₃O | CH₃ |
| CH₃ | CH₃O | CH₃O |
| CH₃ | CH₃O | C₂H₅O |
| CH₃ | CH₃O | CH₃S |
| CH₃ | CH₃O | C₂H₅S |
| CH₃ | CH₃O | benzyl |
| CH₃ | CH₃O | CF=CF₂ |
| CH₃ | CH₃O | C₂F₅ |
| CH₃ | CH₃O | cyclopropyl |
| CH₃ | CH₃O | C₂H₅ |
| CH₃ | CH₃O | CF₃O |
| CH₃ | CH₃O | F₂CHO |
| CH₃ | CH₃O | C₂F₅O |
| CH₃ | CH₃O | CF₃S |
| CH₃ | CH₃O | F₂CHS |
| CH₃ | CH₃O | CF₃ |
| CH₃ | CH₃O | CH₃SO |
| CH₃ | CH₃O | CH₃SO₂ |
| CH₃ | CH₃O | CF₃SO₂ |

Preferred definitions of R¹ are:

| No. | R¹ | No. | R¹ |
|---|---|---|---|
| L1 | OCH₃ | L34 | —C(CH₃)₂—C₂H₅ |
| L2 | OC₂H₅ | L35 | —C(CH₃,C₂H₅)C₂H₅ |
| L3 | O-i-C₃H₇ | L36 | —C(CH₃)₂C₃H₇ |
| L4 | n-C₃H₇ | L37 | —C(CH₃)₂cycloC₆H₁₁ |
| L5 | i-C₃H₇ | L38 | —CH₂—C(CH₃)=CH₂ |
| L6 | n-C₄H₉ | L39 | —CH₂CH=CHCH₃ |
| L7 | i-C₄H₉ | L40 | —CH(CH₃)CH=CHCH₃ |
| L8 | sec-C₄H₉ | L41 | —C(CH₃)₂CH=CHCH₃ |
| L9 | tert-C₄H₉ | L42 | —CH₂C≡CH |
| L10 | n-C₅H₁₁ | L43 | —CH(CH₃)C≡CH |
| L11 | —CH(CH₃)C₃H₇ | L44 | —C(CH₃)₂C≡CH |
| L12 | —CH(C₂H₅)C₂H₅ | L45 | —C(CH₃,C₂H₅)C≡CH |
| L13 | n-C₆H₁₃ | L46 | —C(C₂H₅)₂C≡CH |
| L14 | —CH(CH₃)C₄H₉ | L47 | —CH₂C≡CCH₃ |
| L15 | —CH(C₂H₅)C₃H₇ | L48 | —CH(CH₃)C≡CCH₃ |
| L16 | OC(CH₃)₃ | L49 | —C(CH₃)₂C≡CCH₃ |
| L17 | cyclo-C₃H₅ | L50 | —CH(CH₃)CH₂SCH₃ |
| L18 | cyclo-C₄H₇ | L51 | —C(CH₃)₂CH₂SCH₃ |
| L19 | cyclo-C₅H₉ | L52 | —CH₂CH₂CH₂SCH₃ |
| L20 | cyclo-C₆H₁₁ | L53 | —CH(CH₃)CH₂Cl |
| L21 | cyclo-C₇H₁₃ | L54 | —C(CH₃)₂CH₂Cl |
| L22 | cyclo-C₈H₁₅ | L55 | —CH(CH₃)CH₂OCH₃ |
| L23 | 1-methylcyclohexyl | L56 | —C(CH₃)₂CH₂OCH₃ |
| L24 | 1-ethylcyclohexyl | L57 | —CH₂CH₂CH₂OCH₃ |
| L25 | 3,5-dimethylcyclohexyl | L58 | —CH₂CH₂CH₂N(CH₃)₂ |
| L26 | 3-trifluoromethyl-cyclohexyl | L59 | —CH₂CH₂CH₂N(C₂H₅)₂ |
| | | L60 | cyclopropylmethyl |
| L27 | 1-(cyclopropyl)ethyl | L61 | C(CH₃)₂CH₂F |
| L28 | 1-(cyclopentyl)ethyl | L62 | H |
| L29 | 1-(cyclohexyl)ethyl | L63 | CH₃ |
| L30 | —(CH₂—CH=CH₂) | L64 | C₂H₅ |
| L31 | —CH(CH₃)CH=CH₂ | L65 | cyclopropyl-1-methyl |
| L32 | —C(CH₃)₂C=CH₂ | L66 | cyclopropyl-1-ethyl |
| L33 | —C(CH₃,C₂H₅)CH=CH₂ | | |

The compounds I or the herbicides containing them and their environmentally compatible salts of, for example, alkali metals and alkaline earth metals are very effective in controlling weeds and grass weeds in crops such as wheat, rice, corn, soybean and cotton without damaging the crops, an effect which occurs in particular at low application rates.

The compounds I or the herbicides containing them can be applied, for example, in the form of directly sprayable aqueous solutions, powders, suspensions, including concentrated aqueous, oily or other suspensions or dispersions, emulsions, oil dispersions, pastes, dusting agents, broadcasting agents or granules, by spraying, nebulizing, dusting, broadcasting or pouring. The application forms depend on the intended uses; they should in any case ensure very fine distribution of the novel active ingredients.

The compounds I are suitable in general for the preparation of directly sprayable solutions, emulsions, pastes or oil dispersions. Suitable inert additives are mineral oil fractions having a medium to high boiling point, such as kerosene or diesel oil, as well as coaltar oils and oils of vegetable or animal origin, aliphatic, cyclic and aromatic hydrocarbons, eg. paraffin, tetrahydronaphthalene, alkylated naphthalenes or derivatives thereof, alkylated benzenes or derivatives thereof, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water-dispersible granules by adding water. For the preparation of emulsions, pastes or oil dispersions, the substances, as such or dissolved in an oil or solvent, can be homogenized in water by means of wetting agents, adherents, dispersants or emulsifiers. However, it is also possible to prepare concentrates which consist of active ingredient, wetting agents, adherents, dispersants or emulsifiers and possibly solvent or oil and which are suitable for dilution with water.

Suitable surfactants are the alkali metal, alkaline earth metal and ammonium salts of aromatic sulfonic acids, for example ligninsulfonic acid, phenolsulfonic acid, naphthalenesulfonic acid and dibutylnaphthalenesulfonic acid, and of fatty acids, alkylsulfonates and alkylarylsulfonates, alkylsulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphonol ethers, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetal, sorbitol esters, ligninsulfite waste liquors or methylcellulose.

Powders, broadcasting agents and dusting agents can be prepared by mixing or milling the active substances together with a solid carrier.

Granules, for example coated, impregnated and homogeneous granules, can be prepared by binding the active ingredients to solid carriers. Solid carriers are mineral earths, such as silica gel, silicas, silicates, talc, kaolin, limestone, lime, chalk, bole, loses, clay, dolomite, kieselguhr, calcium sulfate, magnesium sulfate and magnesium oxide, milled plastics, fertilizers, such as ammonium sulfate, ammonium phosphate, ammonium nitrate and ureas, and vegetable products, such as grain flour, bark meal, wood meal and nutshell meal, cellulose powders or other solid carriers.

The formulations contain in general from 0.01 to 95, preferably from 0.5 to 90, % by weight of active ingredient. The active ingredients are used in a purity of from 90 to 100%, preferably from 95 to 100% (according to NMR spectrum).

The novel compounds I may furthermore be formulated, for example, as follows:

I. 20 parts by weight of compound No. 1.031 are dissolved in a mixture which consists of 80 parts by weight of alkylated benzene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100 000 parts by weight of water and finely distributing it therein, an aqueous dispersion which contains 0.02% by weight of the active ingredient is obtained.

II. 20 parts by weight of compound No. 1.031 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100 000 parts by weight of water and finely distributing it thereint an aqueous dispersion which contains 0.02% by weight of the active ingredient is obtained.

III. 20 parts by weight of active ingredient No. 1.031 are dissolved in a mixture which consists of 25 parts by weight of cyclohexanone, 65 parts by weight of a mineral oil fraction boiling within a range from 210° to 280° C. and 10 parts by weight of the adduct of 40 mol of ethylene oxide with 1 mol of castor oil. By pouring the solution into 100 000 parts by weight of water and finely distributing it therein, an aqueous dispersion which contains 0.02% by weight of the active ingredient is obtained.

IV. 20 parts by weight of active ingredient No. 1.031 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20 000 parts by weight of water, a spray liquor which contains 0.1% by weight of the active ingredient is obtained.

V. 3 parts by weight of active ingredient No. 1.031 are mixed with 97 parts by weight of finely divided kaolin. A dusting agent which contains 3% by weight of the active ingredient is obtained in this manner.

VI. 20 parts by weight of active ingredient No. 1.031 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The herbicides or the active ingredients can be applied by the preemergence or postemergence method. If the active ingredients are less well tolerated by certain crops, it is possible to use application methods in which the herbicides are sprayed with the aid of the sprayers in such a way that the leaves of the sensitive crops are as far as possible not affected, while the active ingredients reach the leaves of undesirable plants growing underneath or the uncovered soil surface (post-directed, lay-by).

The application rates of active ingredient are from 0.01 to 5.0, preferably from 0.05 to 2.0, kg/ha of active ingredient (a.i.), depending on the aim of control, the season, the target plants and the stage of growth.

In view of the versatility of the application methods, the novel compounds I or the agents containing them may also be used in a further number of crops for eliminating undesirable plants. Examples of suitable crops are:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycgine max, Gossypium hirmutum* (*Gossypium arboreum, Gossypium herbaceum, Gossypium vitifolium*) *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N. rustica*), *Olea europaea, Oryza sativa, Phaseolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera, Zea mays.*

In order to broaden the action spectrum and to achieve synergiatic effects, the pyridine-2,3-dicarboximides I may be mixed with many members of other groups of herbicidal or growth-regulating active ingredients and may be applied together with these. Examples of suitable herbicidal components for the mixture are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry in the 2-position, for example, a carboxyl or carbimino group, quinolinecarboxylic acid derivatives, imidazolines, sulfonamides, sulfonylureas, aryloxy- and heteroaryloxyphenoxypropionic acids and their salts, esters and amides and others.

It may also be useful to apply the compounds I, alone or in combination with other herbicides or growth regulators, also mixed together with further crop protection agents, for example with pesticides or agents for controlling phytopathogenic fungi or bacteria. The miscibility with mineral salt solutions which are used for eliminating nutrient and trace element deficiencies is also of interest. Nonphytotoxic oils and oil concentrates may also be added.

Preparation of Intermediates a) Diethyl 6-chloro-5-methylpyridine-2,3-dicarboxylate 199.9 g (0.79 mol) of diethyl 5-methylpyridine-2,3-dicarboxylate N-oxide were introduced a little at a time, in the course of 1 hour at from 60° to 70° C, into 1 l of phosphoryl chloride, and the mixture was refluxed for 5 hours. After cooling to 25° C., the reaction mixture was evaporated down under reduced pressure and the residue was taken up in methylene chloride. After filtering through a suction funnel containing silica gel and evaporating down, 148.2 g (69% of theory) of the title compound were obtained as a pale syrup, which subsequently solidified. Mp. 84°–86° C.

$^1$H-NMR (100 MHz), $d_6$-DMSU: 8.3 δ (s/Ar); 2.43 δ (s/CH$_3$)

b) Diethyl 6-fluoro-5-methylpyridine-2,3-dicarboxylate 10 g (0.0368 mol) of compound a) in 15 ml of sulfolane were initially taken, 3.2 g (0.055 mol) of potassium fluoride and 0.3 g of 18-crown-6 were added while stirring, and the mixture was stirred for 2 hours at 160° C. The mixture was cooled to 25° C., after which 250 ml of water were added and the mixture was extracted 3× with methylene chloride. Drying over magnesium sulfate and evaporating down under reduced pressure gave 8 g (85% of theory) of the title compound as a colorless oil.

$^1$H-NMR (100 MHz), CDCl$_3$: 8.1 δ (d/Ar)

Diethyl 4-chloro-6-fluoro-5-methylpyridine-2,3-dicarboxylate and diethyl 4,6-difluoro-5-methylpyridine-2,3-dicarboxylate a) A mixture of 15 g (0.049 mol) of diethyl 4,6-dichloro-5-methylpyridine-2,3-dicarboxyl ate, 3.3 g (0.056 mol) of potassium fluoride and 0.25 g of 18-crown-6 in 80 ml of sulfolane were stirred for 5 hours at 140° C. (corresponding to 0% conversion). After cooling, the reaction mixture was diluted with 200 ml of methyl tert-butyl ether, and the potassium salts were filtered off with suction. The filtrate was extracted 3 times with saturated sodium chloride solution, dried over magnesium sulfate and evaporated down under reduced pressure, 14.2 g of a yellowish oil being obtained. 3.55 g (27% of theory) of the difluoro title compound of boiling point 130°–138° C./0.5 mbar and 8.39 g (53% of theory) of the chlorofluoro title compound of boiling point 148°–155° C./0.5 mbar were isolated therefrom by distillation.

b) 7.21 g (53% of theory) of the difluoro compound and 1.17 g (8.3% of theory) of the chlorofluoro compound were obtained under the same reaction conditions but with the use of 8.5 g (0.148 mol) of potassium fluoride and with stirring for 14 hours at 160° C.

Diethyl 5-methoxypyridine-2,3-dicarboxylate 83 g (1.05 mol) of pyridine were added to 221.5 g (1.0 mol) of diethyl 2-amino-3-chloromaleate in 250 ml of glacial acetic acid at 80° C. while stirring. 90 g (1.05 mol) of mathoxyacrolein were then added at 120° C. in the course of 30 minutes, gentle refluxing being established without heating. The reaction mixture was stirred for 3 hours at 120° C. and then evaporated down under reduced pressure, water was added to the residue and the mixture was extracted with methylene chloride. After filtration of active carbon, drying, filtration over neutral alumina with suction and evaporating down under reduced pressure, 190 g (75% of theory) of the title compound were obtained as a pale yellow syrup.

$^1$H-NMR (100 MHz), CDCl$_3$: 8.4 δ 7.48 δ (s/Ar); 3.85 δ (s/CH$_3$O)

6-Fluoropyridine-2,3-dicarboxylic anhydride

A mixture of 36.7 g (0.2 mol) of 6-chloropyridine-2,3-dicarboxylic anhydride, 17.4 g (0.3 mol) of potassium fluoride and 1 g of 18-crown-6 in 200 ml of propionitrile were stirred for 10 hours while refluxing. After cooling, the reaction mixture was filtered with suction and the residue was washed with methylene chloride. The filtrate was evaporated down under reduced pressure and stirred with a 2:1 methyl tert-butyl ether/pentane mixture, and the product was filtered off with suction and dried. 25.3 g (76% of theory) of the title compound of melting point 106° C. (decomposition) were obtained.

Preparation Examples for the Compounds I 1. 5-chloro-6-methylpyridine-N-tert-butyl-2,3-dicarboximide a) Diethyl 5-amino-6-methylpyridine-2,3-dicarboxylate 56.9 g (1.065 mol) of iron powder in 200 ml of glacial acetic acid were initially taken and were heated to 70° C. while stirring, and a solution of 100 g (0.355 mol) of diethyl 6-methyl-5-nitropyridine-2,3-dicarboxylate (EP 227 932) in 700 ml of glacial acetic acid was added in the course of 20 minutes. Stirring was carried out for 2 hours, after which a further 25.2 g (0.45 mol) of iron powder in 200 ml of glacial acetic acid were added and stirring was continued for a further hour at 70° C. The mixture was cooled to 25° C., the precipitate was filtered off with suction and the filtrate was evaporated down under reduced pressure, after which the residue was taken up in methylene chloride, extracted in succession with water, saturated sodium bicarbonate solution and sodium chloride solution, dried over magnesium sulfate and filtered off with suction over a suction filter containing silica gel. 49 g (55% of theory) of the title compound were isolated as a yellow resin from fractions 3 and 4 after they had been evaporated down.

$^1$H-NMR 100 MHz (CDCl$_3$): 7.13 6 δ (s/Ar), 4.05 δ (s/NH$_2$)

b) Diethyl 5-chloro-6-methylpyridine-2,3-dicarboxylate 5.8 g (0.2 mol) of the above compound a) were introduced a little at a time into 200 ml of concentrated hydrochloric acid while stirring at 20° C., and the mixture was then cooled to 0° C. 31.7 g (0.46 mol) of sodium nitrite, dissolved in 60 ml of water, were added to this solution in the course of 30 minutes at from 0° to 50° C., and stirring was continued for a further 30 minutes. The suspension obtained was then introduced into a beaker with 29.6 g (0.5 mol) of sodium chloride, 63.2 g (0.25 mol) of copper sulfate 5-hydrate and 120 ml of water and was stirred for 2 hours at 25° C. Extraction was effected with methylene chloride, purification was carried out in succession with saturated sodium bicarbonate solution and sodium chloride solution, drying was effected over magnesium sulfate and the product was filtered off with suction over a suction filter containing silica gel. Evaporating down gave 44.2 g (71% of theory) of the title compound having $n_D^{23}$=1.5150.

c) 5-Chloro-6-methylpyridine-2,3-dicarboxylic anhydride 9.5 g (0.038 mol) of the above compound b) in a mixture of 3.02 g (0.075 mol) of sodium hydroxide in 20 ml of water and 5 ml of ethanol were refluxed for 2 hours. The mixture was cooled, after which the dicarboxylic acid salt was precipitated with 500 ml of acetone; 9.1 g (93% of theory) of product of melting point >240° C. were obtained.

Of this, 9 g (0.035 mol) in 100 ml of 1,2-dichloroethane were initially taken, 6.8 g (0.09 mol) of acetyl chloride were added dropwise and the mixture was refluxed for 8 hours. The mixture was cooled and then filtered with suction, the residue was washed with methylene chloride and the filtrate was evaporated down under reduced pressure. 5.8 g (85% of theory) of the title compound of melting point 140°–141° C. were obtained.

d) End product 9.9 g (0.05 mol) of compound c) in 150 ml of 1,2-dichloroethane were initially taken, 4.0 g (0.06 mol) of tert-butylamine were added dropwise and stirring was carried out for 3 hours at 70° C. The mixture was cooled to 25° C., after which 8.2 g (0.069 mol) of thionyl chloride were added and stirring was carried out for 14 hours. 150 ml of methylene chloride and 150 ml of ice water were added in succession and the phases were separated. Washing and drying as in b) and evaporating down gave 10 g (79% of theory) of 5-chloro-6-methylpyridine-N-tert-butyl-2,3-dicarboximide of melting point 114°–115° C. (active ingredient Example 1.031).

2. 5-fluoropyridine-N-1-cyclopropylethyl-2,3-dicarboximide

A mixture of 19.5 g (0.0778 mol) of 5-chloropyridine-N-1-cyclopropylethyl-2,3-dicarboximide, 9.1 g (0.156 mol) of potassium fluoride and 0.4 g of 18-crown-6 in 50 ml of sulfolane were stirred for 6 hours at 180° C. The mixture was cooled and then poured onto 500 ml of ice water, and the resulting precipitate was filtered off with suction and washed with water. The residue was taken up in methylene chloride, stirred over active carbon, dried over magnesium sulfate and then passed with suction through neutral alumina. Evaporating down under reduced pressure gave 14.1 g (78% of theory) of the title compound of melting point 95°–98° C. (active ingredient Example 1.041).

3. 5,6-Difluoropyridine-N-1-cyclopropylethyl-2,3-dicarboximide

A mixture of 7.2 g (0.027 mol) of 6-chloro-5-fluoropyridins-N-1-cyclopropylethyl-2,3-dicarboximide, 2.3 g (0.04 mol) of potassium fluoride and 0.1 g of 18-crown-6 in 50 ml of sulfolane were stirred for 3 hours at 150° C. Working up similarly to Example 2, with filtration with suction over silica gel, gave 4.8 g (71% of theory) of the title compound of melting point 52°–54° C. (active ingredient Example 1.046).

The pyridine-2,3-dicarboximides of the formula I which are listed in Table 1 were obtained similarly to these processes described in Examples 1 to 3 and for the intermediates. Novel pyridine-2,3-dicarboxylic anhydrides and pyridine-2,3-dicarboxylates are shown in Tables 2 and 3.

TABLE 1

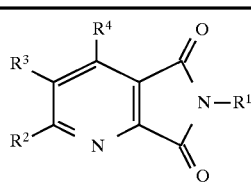

| No. | R¹ | R² | R³ | R⁴ | Mp. (°C.) |
|---|---|---|---|---|---|
| 1.001 | tert-C₄H₉ | Cl | CH₃O | H | 198–200 |
| 1.002 | tert-C₄H₉ | H | CH₃O | H | 127–129 |
| 1.003 | cyclopropyl | H | CH₃O | H | 166–169 |
| 1.004 | tert-C₄H₉ | CH₃O | CH₃O | H | 213–215 |
| 1.005 | 1-(cyclopropyl)ethyl | H | CH₃O | H | 101–102 |
| 1.006 | tert-C₄H₉ | H | CH₃O | Cl | |
| 1.007 | tert-C₄H₉ | Cl | Cl | H | 87–89 |
| 1.008 | tert-C₄H₉ | Cl | Cl | Cl | 137–138 |
| 1.009 | 1-(cyclopropyl)ethyl | CH₃O | Cl | Cl | |
| 1.010 | tert-C₄H₉ | H | Cl | H | 104–105 |
| 1.011 | tert-C₄H₉ | H | CF₃ | H | 198–204 |
| 1.012 | tert-C₄H₉ | CH₃O | Cl | H | 177–179 |
| 1.013 | tert-C₄H₉ | F | H | H | 92–95 |
| 1.014 | sec-C₄H₉ | CH₃O | CH₃O | H | 195–197 |
| 1.015 | sec-C₄H₉ | Cl | CH₃O | H | 179–181 |
| 1.016 | sec-C₄H₉ | F | H | H | 40–42 |
| 1.017 | 1-(cyclopropyl)ethyl | CH₃O | CH₃O | H | 192–194 |

TABLE 1-continued

| No. | R¹ | R² | R³ | R⁴ | Mp. (°C.) |
|---|---|---|---|---|---|
| 1.018 | 1-(cyclopropyl)ethyl | Cl | CH₃O | H | 178–180 |
| 1.019 | 1-(cyclopropyl)ethyl | Cl | Cl | H | 109–111 |
| 1.020 | 1-(cyclopropyl)ethyl | CH₃O | Cl | Cl | |
| 1.021 | 1-(cyclopropyl)ethyl | H | Cl | H | 56–60 |
| 1.022 | 1-(cyclopropyl)ethyl | F | H | H | 92–95 |
| 1.023 | i-C₃H₇ | CH₃O | CH₃O | H | 244–246 |
| 1.024 | i-C₃H₇ | Cl | CH₃O | H | 206–208 |
| 1.025 | i-C₃H₇ | H | Cl | H | 103–106 |
| 1.026 | i-C₃H₇ | F | H | H | 80–83 |
| 1.027 | i-C₃H₇ | F | CH₃ | H | 117–118 |
| 1.028 | tert-C₄H₉ | F | CH₃ | H | 133–134 |
| 1.029 | tert-C₄H₉ | CH₃ | CN | H | 148–150 |
| 1.030 | i-C₃H₇ | CH₃ | CN | H | 171–172 |
| 1.031 | tert-C₄H₉ | CH₃ | Cl | H | 114–115 |
| 1.032 | 1-(cyclopropyl)ethyl | F | CH₃O | H | 108–110 |
| 1.033 | i-C₃H₇ | F | CH₃O | H | 129–130 |
| 1.034 | tert-C₄H₉ | F | CH₃O | H | 136–140 |
| 1.035 | i-C₃H₇ | Cl | Cl | H | 85–90 |
| 1.036 | tert-C₄H₉ | Cl | CF₃ | H | 76–77 |
| 1.037 | i-C₃H₇ | CH₃ | Cl | H | 122–124 |
| 1.038 | 1-(cyclopropyl)ethyl | CH₃ | Cl | H | 61–62 |
| 1.039 | i-C₃H₇ | F | Cl | H | 100–103 |
| 1.040 | tert-C₄H₉ | F | Cl | Cl | |
| 1.041 | 1-(cyclopropyl)ethyl | H | F | H | 95–98 |
| 1.042 | tert-C₄H₉ | H | F | H | 55–56 |
| 1.043 | (−)1-(cyclopropyl)ethyl | CH₃ | Cl | H | 60–63 |
| 1.044 | (+)1-(cyclopropyl)ethyl | CH₃ | Cl | H | 66–67 |
| 1.045 | 1-(cyclopropyl)ethyl | CH₃O | F | H | 87–88 |
| 1.046 | 1-(cyclopropyl)ethyl | F | F | H | 52–54 |
| 1.047 | 1-(cyclopropyl)ethyl | Cl | F | H | 77–78 |
| 1.048 | 1-(cyclopropyl)ethyl | Cl | H | Cl | 99–102 |
| 1.049 | tert-C₄H₉ | Cl | H | Cl | 132–134 |
| 1.050 | i-C₃H₇ | H | H | Cl | 104–105 |
| 1.051 | 1-(cyclopropyl)ethyl | H | H | Cl | 78–80 |
| 1.052 | tert-C₄H₉ | H | H | Cl | 141–142 |
| 1.053 | tert-C₄H₉ | H | H | CH₃O | 201–202 |
| 1.054 | 1-(cyclopropyl)ethyl | CH₃O | H | CH₃O | 225–228 |
| 1.055 | tert-C₄H₉ | H | H | F | 85–88 |
| 1.056 | tert-C₄H₉ | CH₃ | CH₃O | H | |
| 1.057 | 1-(cyclopropyl)ethyl | CH₃ | CH₃O | H | |
| 1.058 | tert-C₄H₉ | CH₃ | CH₃O | Cl | |
| 1.059 | tert-C₄H₉ | CH₃ | CH₃O | F | |
| 1.060 | tert-C₄H₉ | CH₃ | CH₃ | Cl | |
| 1.061 | tert-C₄H₉ | CH₃ | CH₃ | F | |
| 1.062 | 1-(cyclopropyl)ethyl | CH₃ | CH₃ | F | |
| 1.063 | tert-C₄H₉ | Cl | CH₃O | Cl | |
| 1.064 | 1-(cyclopropyl)ethyl | Cl | CH₃O | F | |
| 1.065 | H | F | H | H | |
| 1.066 | H | Cl | F | H | |
| 1.067 | H | H | H | F | |
| 1.068 | H | F | Cl | F | |
| 1.069 | H | F | Cl | H | |
| 1.070 | i-C₃H₇ | Cl | Cl | Cl | 148–155 |
| 1.071 | 1-(cyclopropyl)ethyl | Cl | Cl | Cl | 114–115 |
| 1.072 | tert-C₄H₉ | Cl | CH₃ | Cl | 150–152 |
| 1.073 | 1-(cyclopropyl)ethyl | Cl | CH₃ | Cl | 106–108 |
| 1.074 | i-C₃H₇ | Cl | CH₃ | Cl | 149–153 |
| 1.075 | 1-(cyclopropyl)ethyl | CH₃O | CH₃ | CH₃O | 109–113 |
| 1.076 | tert-C₄H₉ | CH₃O | CH₃ | CH₃O | 130–134 |
| 1.077 | tert-C₄H₉ | CH₃O | H | Cl | 107–110 |
| 1.078 | 1-(cyclopropyl)ethyl | F | CH₃ | H | 66–68 |
| 1.079 | tert-C₄H₉ | Cl | CH₃O | Cl | 119–122 |
| 1.080 | tert-C₄H₉ | CH₃ | Cl | Cl | 110–113 |

TABLE 2

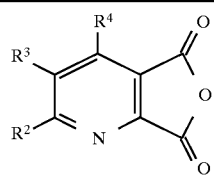

IIa'

| No. | $R^2$ | $R^3$ | $R^4$ | Physical data - Mp. (°C.) $^1$H-NMR, 200 MHz, δ [ppm] in CDCl$_3$ |
|---|---|---|---|---|
| 2.001 | H | H | F | |
| 2.002 | F | F | H | |
| 2.003 | F | H | H | |
| 2.004 | F | H | F | 106 decomposition |
| 2.005 | F | Cl | H | |
| 2.006 | F | Cl | Cl | |
| 2.007 | Cl | F | H | |
| 2.008 | Cl | F | Cl | |
| 2.009 | CH$_3$ | F | H | |
| 2.010 | CH$_3$O | F | H | |
| 2.011 | CH$_3$ | H | F | |
| 2.012 | CH$_3$O | H | F | |
| 2.013 | F | CH$_3$ | F | |
| 2.014 | F | CH$_3$O | F | |
| 2.015 | F | H | CH$_3$ | |
| 2.016 | F | H | CH$_3$O | |
| 2.017 | F | F | CH$_3$O | |
| 2.018 | F | CH$_3$ | H | 90–95 |
| 2.019 | H | CH$_3$ | F | |
| 2.020 | F | CH$_3$O | H | |
| 2.021 | H | CH$_3$O | F | |
| 2.022 | F | Cl | CH$_3$ | |
| 2.023 | F | F | CH$_3$ | |
| 2.024 | F | Cl | CH$_3$O | |
| 2.025 | CH$_3$ | Cl | H | 140–141 |
| 2.026 | CH$_3$ | CH$_3$O | H | |
| 2.027 | H | CH$_3$O | H | 36–39 |
| 2.028 | Cl | CH$_3$O | H | 165–170 decomposition |
| 2.029 | CH$_3$O | CH$_3$O | H | 210–214 |
| 2.030 | H | CF$_3$ | H | 70 |
| 2.031 | CH$_3$ | CN | H | CH$_3$: 3/05 (s/3), Ar: 8.58 (s/1) |
| 2.032 | CH$_3$O | Cl | H | |
| 2.033 | Cl | Cl | H | |
| 2.034 | Cl | Cl | Cl | 176–181 |
| 2.035 | Cl | CH$_3$ | Cl | 160–161 |
| 2.036 | CH$_3$O | CH$_3$ | CH$_3$O | CH$_3$ 2.15, CH$_3$O 4.15, 4.35 |
| 2.037 | CH$_3$O | H | Cl | 95–97 |
| 2.038 | CH$_3$ | Cl | Cl | 199–201 |

TABLE 3

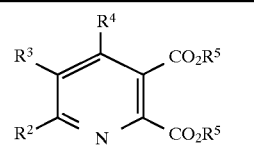

Va'–a'''

| No. | $R^2$ | $R^3$ | $R^4$ | $R^5$ | Physical data - Bp. [°C.]/mbar; Fp (°C.) $^1$H-NMR, 400 MHz, δ [ppm] in CDCl$_3$ |
|---|---|---|---|---|---|
| 3.001 | H | H | F | CH$_3$ | |
| 3.002 | F | F | H | CH$_3$ | |
| 3.003 | F | H | H | CH$_3$ | |
| 3.004 | F | H | F | CH$_3$ | |
| 3.005 | F | Cl | H | CH$_3$ | |
| 3.006 | F | Cl | Cl | CH$_3$ | |
| 3.007 | Cl | F | H | CH$_3$ | |
| 3.008 | Cl | F | Cl | CH$_3$ | |
| 3.009 | CH$_3$ | F | H | CH$_3$ | |
| 3.010 | CH$_3$O | F | H | CH$_3$ | |
| 3.011 | CH$_3$ | H | F | CH$_3$ | |
| 3.012 | CH$_3$O | H | F | CH$_3$ | |
| 3.013 | F | CH$_3$ | F | CH$_3$ | |
| 3.014 | F | CH$_3$O | F | CH$_3$ | |
| 3.015 | F | H | CH$_3$ | CH$_3$ | |
| 3.016 | F | H | CH$_3$O | CH$_3$ | |
| 3.017 | F | F | CH$_3$O | CH$_3$ | |
| 3.018 | F | CH$_3$ | H | CH$_3$ | |
| 3.019 | H | CH$_3$ | F | CH$_3$ | |
| 3.020 | F | CH$_3$O | H | CH$_3$ | |
| 3.021 | H | CH$_3$O | F | CH$_3$ | |
| 3.022 | F | Cl | CH$_3$ | CH$_3$ | |
| 3.023 | F | F | CH$_3$ | CH$_3$ | |
| 3.024 | F | H | F | C$_2$H$_5$ | |
| 3.025 | F | F | H | C$_2$H$_5$ | |
| 3.026 | F | H | H | C$_2$H$_5$ | 112–115/0.3 |
| 3.027 | F | H | F | C$_2$H$_5$ | 88–93/0.1 |
| 3.028 | F | Cl | H | C$_2$H$_5$ | 131–133/0.5 |
| 3.029 | F | Cl | Cl | C$_2$H$_5$ | |
| 3.030 | Cl | F | H | C$_2$H$_5$ | |
| 3.031 | Cl | F | Cl | C$_2$H$_5$ | |
| 3.032 | CH$_3$ | F | H | C$_2$H$_5$ | |
| 3.033 | CH$_3$O | F | H | C$_2$H$_5$ | |
| 3.034 | CH$_3$ | H | F | C$_2$H$_5$ | |
| 3.035 | CH$_3$O | H | F | C$_2$H$_5$ | |
| 3.036 | F | CH$_3$ | F | C$_2$H$_5$ | 130–138/0.5 |
| 3.037 | F | CH$_3$O | F | C$_2$H$_5$ | |
| 3.038 | F | H | CH$_3$ | C$_2$H$_5$ | |
| 3.039 | F | H | CH$_3$O | C$_2$H$_5$ | |
| 3.040 | F | F | CH$_3$O | C$_2$H$_5$ | |
| 3.041 | F | CH$_3$ | H | C$_2$H$_5$ | CH$_3$: 2.36 (s/1), Ar: 8.1 (d/1) |
| 3.042 | H | CH$_3$ | F | C$_2$H$_5$ | |
| 3.043 | F | CH$_3$O | H | C$_2$H$_5$ | |
| 3.044 | H | CH$_3$O | F | C$_2$H$_5$ | |
| 3.045 | F | Cl | CH$_3$ | C$_2$H$_5$ | |
| 3.046 | F | F | CH$_3$ | C$_2$H$_5$ | |
| 3.047 | F | Cl | CH$_3$O | CH$_3$ | |
| 3.048 | F | Cl | CH$_3$O | C$_2$H$_5$ | |
| 3.049 | H | CF$_3$ | H | C$_2$H$_5$ | Ar: 8.42 (d/1); 9.0 (d/1) |
| 3.050 | H | Cl | H | C$_2$H$_5$ | Ar: 8.17 (d/1); 8.7 (d/1) |
| 3.051 | F | CH$_3$ | Cl | C$_2$H$_5$ | 148–155/0.5 |
| 3.052 | F | CH$_3$ | Cl | CH$_3$ | |
| 3.053 | H | F | H | C$_2$H$_5$ | 93–99/0.3 |
| 3.054 | Cl | Cl | H | CH$_3$ | 32–34 |
| 3.055 | Cl | Cl | H | C$_2$H$_5$ | 56–58 |
| 3.056 | Cl | Cl | Cl | CH$_3$ | |
| 3.057 | Cl | Cl | Cl | C$_2$H$_5$ | $n_D^{20}$ = 1.5404 |
| 3.058 | Cl | H | Cl | CH$_3$ | |
| 3.059 | Cl | H | Cl | C$_2$H$_5$ | Ar 7.6 (s/1) |
| 3.060 | Cl | CH$_3$ | Cl | CH$_3$ | |
| 3.061 | Cl | CH$_3$ | Cl | C$_2$H$_5$ | ArCH$_3$ 2.60 (s/3) |
| 3.062 | CH$_3$ | Cl | H | C$_2$H$_5$ | $n_D^{23}$ = 1.5150 |
| 3.063 | H | CH$_3$O | H | C$_2$H$_5$ | (100 MHz) 8.4; 7.48 (s/Ar) |
| 3.064 | CH$_3$ | Cl | Cl | C$_2$H$_5$ | CH$_3$ 2.8 |
| 3.065 | CH$_3$O | CH$_3$ | CH$_3$O | CH$_3$ | 1.5150 |
| 3.066 | CH$_3$ | Cl | Cl | C$_2$H$_5$ | CH$_3$ 2.8 (s/3) |

Use Examples

The herbicidal action of the pyridine-2,3-dicarboximides of the formula I could be demonstrated by greenhouse experiments:

the culture vessels used were plastic pots containing loamy sand with about 3.0% of humus as a substrate. The seeds of the teat plants were sown separately according to species.

In the preemergence treatment, the active ingredients suspended or emulsified in water were applied directly after sowing by means of finely distributing nozzles. The vessels were lightly sprinkler-irrigated in order to promote germination and growth and were then covered with transparent plastic covers until the plants had emerged. This covering ensures uniform germination of the test plants, unless this has been adversely affected by the active ingredients.

For the postemergence treatment, the test plants were grown to a height of growth of from 3 to 15 cm, depending on the form of growth, before being treated with the active ingredients suspended or emulsified in water. For this purpose, the test plants were either directly sown and grown in the same vessels or they were initially grown separately as seedlings and transplanted into the test vessels a few days before the treatment. The application rate for the postemergence treatment was 0.5 and 0.25 kg/ha of active ingredient.

The plants were kept at 10°–25° C. or 20°–35° C., depending on the species. The test period extended over from 2 to 4 weeks. During this time, the plants were tended and their reaction to the individual treatments was evaluated.

The herbicidal action was rated on a scale of 0 to 100. 100 means no emergence of the plants or complete destruction of at least the above-ground parts and 0 means no damage or normal course of growth.

The plants used in the greenhouse experiments consisted of the following species:

| Abbreviation | Botanical name | Common name |
|---|---|---|
| ABUTH | *Abutilon theophrasti* | Velvetleaf |
| AMARE | *Amaranthus retroflexus* | Redroot pigweed |
| CHEAL | *Chenopodium album* | Common lambsquarters |
| GALAP | *Galium aparine* | Catchweed bedstraw |
| IPOSS | *Ipomoea ssp.* | Morningglory species |
| STEME | *Stellaria media* | Chickweed |

The results (cf. Tables I to III below) show the superior herbicidal action of the novel compounds in comparison with the Comparative Examples A, B and C disclosed in EP-A 422 456.

TABLE I

Examples for controlling undesirable plants with postemergence application of 0.5 kg a.i./ha in the greenhouse

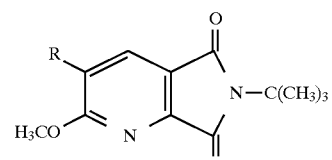

| R | $O-CH_3$ | $C_2H_5$ |
|---|---|---|
| Example No. | 1.002 | A |
| Test plants | Damage in % | |
| ABUTH | 100 | 0 |

TABLE I-continued

Examples for controlling undesirable plants with postemergence application of 0.5 kg a.i./ha in the greenhouse

| AMARE | 100 | 10 |
|---|---|---|
| IPOSS | 100 | 0 |

TABLE II

Examples for controlling undesirable plants with postemergence application of 0.5 kg a.i./ha in the greenhouse

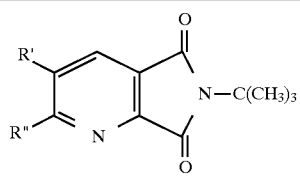

| R | Cl | H |
|---|---|---|
| Example No. | 1.012 | B |
| Test plants | Damage in % | |
| ABUTH | 100 | 75 |
| IPOSS | 100 | 75 |
| STEME | 98 | 60 |

TABLE III

Examples for controlling undesirable plants with postemergence application of 0.5 kg and 0.25 kg a.i./ha in the greenhouse

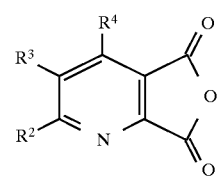

| R' | Cl | Cl | $CH_3$ | $CH_3$ |
|---|---|---|---|---|
| R" | $CH_3$ | $CH_3$ | Cl | Cl |
| Example No. | 1.031 | 1.031 | C | C |
| Application rate (kg a.i./ha) | 0.5 | 0.25 | 0.5 | 0.25 |
| Test plants | Damage in % | | | |
| ABUTH | 100 | 100 | 30 | 30 |
| CHEAL | 100 | 100 | 100 | 95 |
| GALAP | 98 | 90 | 98 | 75 |

We claim:

1. A pyridine-2,3-dicarboxylic anhydride of the formula IIa'

$$\text{IIa'}$$

where one of the radicals $R^2$, $R^3$ or $R^4$ is fluorine and the other radicals are each hydrogen, fluorine, chlorine, $C_1$–$C_3$-alkyl, $C_1$–$C_3$-alkoxy, trifluoromethoxy, chlorodifluoromethoxy, methylthio, trifluoromethylthio, chlorodifluoromethylthio or mothylaulfonyl, with the exception of 5-fluoro- and 4,5,6-trifluoropyridine-2,3-dicarboxylic anhydride.

2. 6-Fluoropyridine-2,3-dicarboxylic anhydride and 5,6-difluoropyridine-2,3-dicarboxylic anhydride.

\* \* \* \* \*

UNITED STATES PATENT AND TRADEMARK OFFICE
CERTIFICATE OF CORRECTION

PATENT NO.: 5,840,904

DATED: November 24, 1998

INVENTOR(S): HAMPRECHT et al.

It is certified that error appears in the above-identified patent and that said Letters Patent is hereby corrected as shown below:

On the title page, insert the following:

--[30]   Foreign Application Priority Data
Dec. 22, 1993   [DE]   Germany ............. 43 43 923.3--.

In the abstract, line 15 after formula I, "trifluoromathyl" should be --trifluoromethyl--.

In the abstract, line 19 after formula I, "$C_2$-$C_5$alky-nyloxy" should be --$C_2$-$C_5$-alkynyloxy--.

Col. 36, claim 1, line 62, "mothylaulfonyl" should be --methylsulfonyl--.

Signed and Sealed this

Twenty-seventh Day of April, 1999

Attest:

Q. TODD DICKINSON

*Attesting Officer*   *Acting Commissioner of Patents and Trademarks*